US008909530B2

(12) United States Patent
Wexler et al.

(10) Patent No.: US 8,909,530 B2
(45) Date of Patent: Dec. 9, 2014

(54) APPARATUS, METHOD, AND COMPUTER READABLE MEDIUM FOR EXPEDITED TEXT READING USING STAGED OCR TECHNIQUE

(71) Applicants: Yonatan Wexler, Jerusalem (IL); Amnon Shashua, Mevasseret Zion (IL)

(72) Inventors: Yonatan Wexler, Jerusalem (IL); Amnon Shashua, Mevasseret Zion (IL)

(73) Assignee: OrCam Technologies Ltd. (IL)

( * ) Notice: Subject to any disclaimer, the term of this patent is extended or adjusted under 35 U.S.C. 154(b) by 0 days.

(21) Appl. No.: 14/136,438

(22) Filed: Dec. 20, 2013

(65) Prior Publication Data

US 2014/0278430 A1 Sep. 18, 2014

Related U.S. Application Data

(60) Provisional application No. 61/799,649, filed on Mar. 15, 2013, provisional application No. 61/830,122, filed on Jun. 2, 2013.

(51) Int. Cl.
*G10L 13/02* (2013.01)

(52) U.S. Cl.
USPC .......................................... 704/260; 382/140

(58) Field of Classification Search
USPC ....................................................... 704/260
See application file for complete search history.

(56) References Cited

U.S. PATENT DOCUMENTS

| 6,115,482 A | 9/2000 | Sears et al. |
| 6,205,427 B1 * | 3/2001 | Itoh et al. ...................... 704/260 |
| 2005/0208457 A1 | 9/2005 | Fink et al. |
| 2006/0017810 A1 | 1/2006 | Kurzweil et al. |
| 2010/0088099 A1 * | 4/2010 | Kurzweil et al. ............. 704/260 |
| 2011/0060590 A1 * | 3/2011 | Katae et al. ................... 704/260 |
| 2012/0212593 A1 | 8/2012 | Na'aman et al. |
| 2013/0169536 A1 | 7/2013 | Wexler et al. |
| 2013/0271584 A1 | 10/2013 | Wexler et al. |

FOREIGN PATENT DOCUMENTS

EP 2065871 6/2009

OTHER PUBLICATIONS

U.S. Appl. No. 14/135,727, filed Dec. 20, 2013, entitled "Systems and Method for Audible Facial Recognition,".
U.S. Appl. No. 14/137,033, filed Dec. 20, 2013, entitled "Apparatus and Method for Providing Failed-Attempt Feedback Using a Camera on Glasses,".
U.S. Appl. No. 14/137,263, filed Dec. 20, 2013, entitled "Apparatus and Method for Executing System Commands Based on Captured Image Data,".

(Continued)

*Primary Examiner* — Daniel D Abebe
(74) *Attorney, Agent, or Firm* — Finnegan, Henderson, Farabow, Garrett & Dunner LLP

(57) ABSTRACT

A system and method are provided for accelerating machine reading of text. In one embodiment, the system comprises at least one processor device. The processor device is configured to receive at least one image of text to be audibly read. The text includes a first portion and a second portion. The processor device is further configured to initiate optical character recognition (OCR) to recognize the first portion. The processor device is further configured to initiate an audible presentation of the first portion prior to initiating OCR of the second portion, and simultaneously perform OCR to recognize the second portion of the text to be audibly read during presentation of at least part of the first portion. The processor device is further configured to automatically cause the second portion of the text to be audibly presented immediately upon completion of the presentation of the first portion.

22 Claims, 30 Drawing Sheets

(56) References Cited

OTHER PUBLICATIONS

U.S. Appl. No. 14/135,757, filed Dec. 20, 2013, entitled "Systems and Methods for Automatic Control of a Continuous Action,".
U.S. Appl. No. 14/137,373, filed Dec. 20, 2013, entitled "Apparatus and Method for Automatic Action Selection Based on Image Context,".
U.S. Appl. No. 14/135,762, filed Dec. 20, 2013, entitled "Systems and Methods for Performing a Triggered Action,".
U.S. Appl. No. 14/137,328, filed Dec. 20, 2013, entitled "Apparatus and Method for Performing Actions Based on Captured Image Data,".
U.S. Appl. No. 14/135,859, filed Dec. 20, 2013, entitled "Apparatus Connectable to Glasses,".
U.S. Appl. No. 14/137,446, filed Dec. 20, 2013, entitled "Apparatus and Method for Hierarchical Object Identification Using a Camera on Glasses,".
U.S. Appl. No. 14/135,928, filed Dec. 20, 2013, entitled "Systems and Methods for Processing Images,".
U.S. Appl. No. 14/135,775, filed Dec. 20, 2013, entitled "Systems and Methods for Providing Feedback Based on the State of an Object,".
U.S. Appl. No. 14/137,522, filed Dec. 20, 2013, entitled "Apparatus and Method for Using Background Change to Determine Context,".
U.S. Appl. No. 14/136,545, filed Dec. 20, 2013, entitled "Apparatus, Method, and Computer Readable Medium for Recognizing Text on a Curved Surface,".
U.S. Appl. No. 14/137,384, filed Dec. 20, 2013, entitled "Systems and Methods for Audibly Presenting Textual Information Included in Image Data,".
U.S. Appl. No. 14/136,876, filed Dec. 20, 2013, entitled "Apparatus and Method for Analyzing Images,".
Karacs, Kristof et al., "Bionic Eyeglass: An Audio Guide for Visually Impaired," Biomedical Circuits and Systems Conference, 2006, BIOCAS 2006, IEEE, Piscataway, NJ, Nov. 29, 2006, p. 190-193.
Lai, Chin-Lun et al., "An Integrated Portable Vision Assistant Agency for the Visual Impaired People," 2009 IEEE International Conference on Control and Automation, Christchurch, New Zealand, Dec. 9-11, 2009 (6 pages).

* cited by examiner

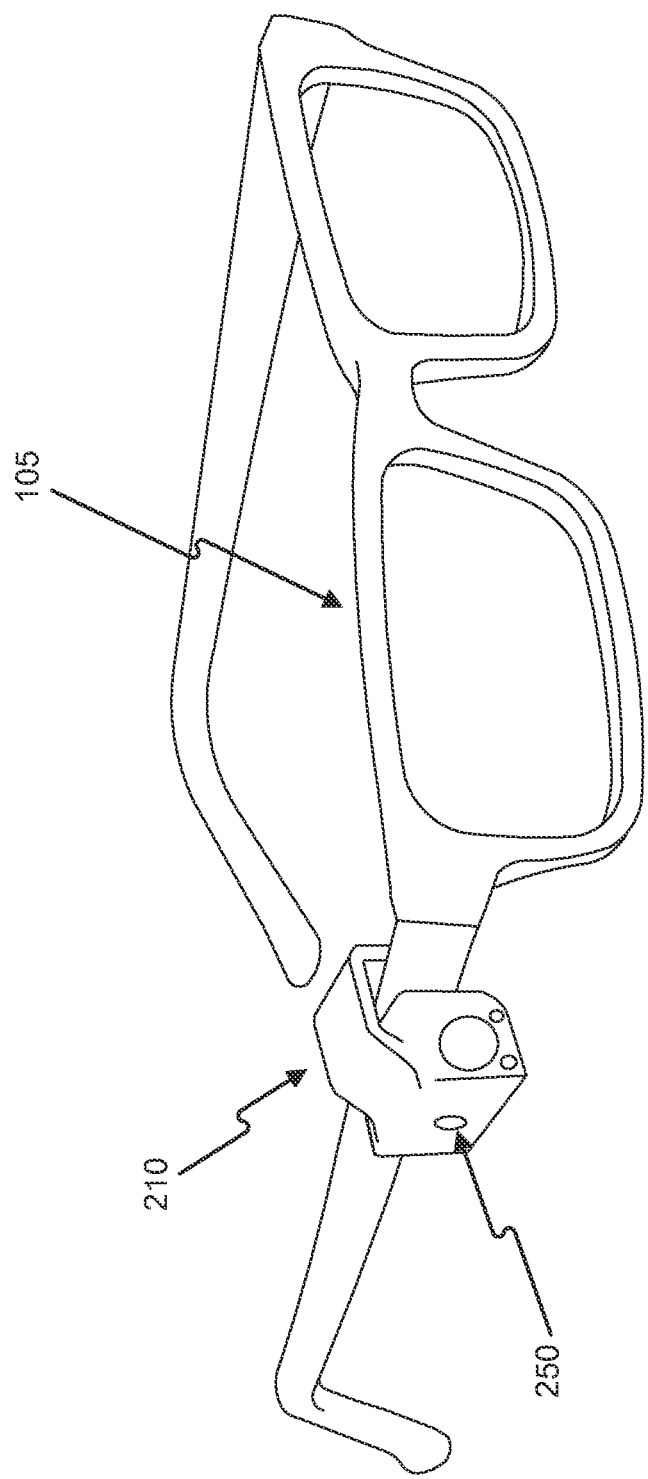

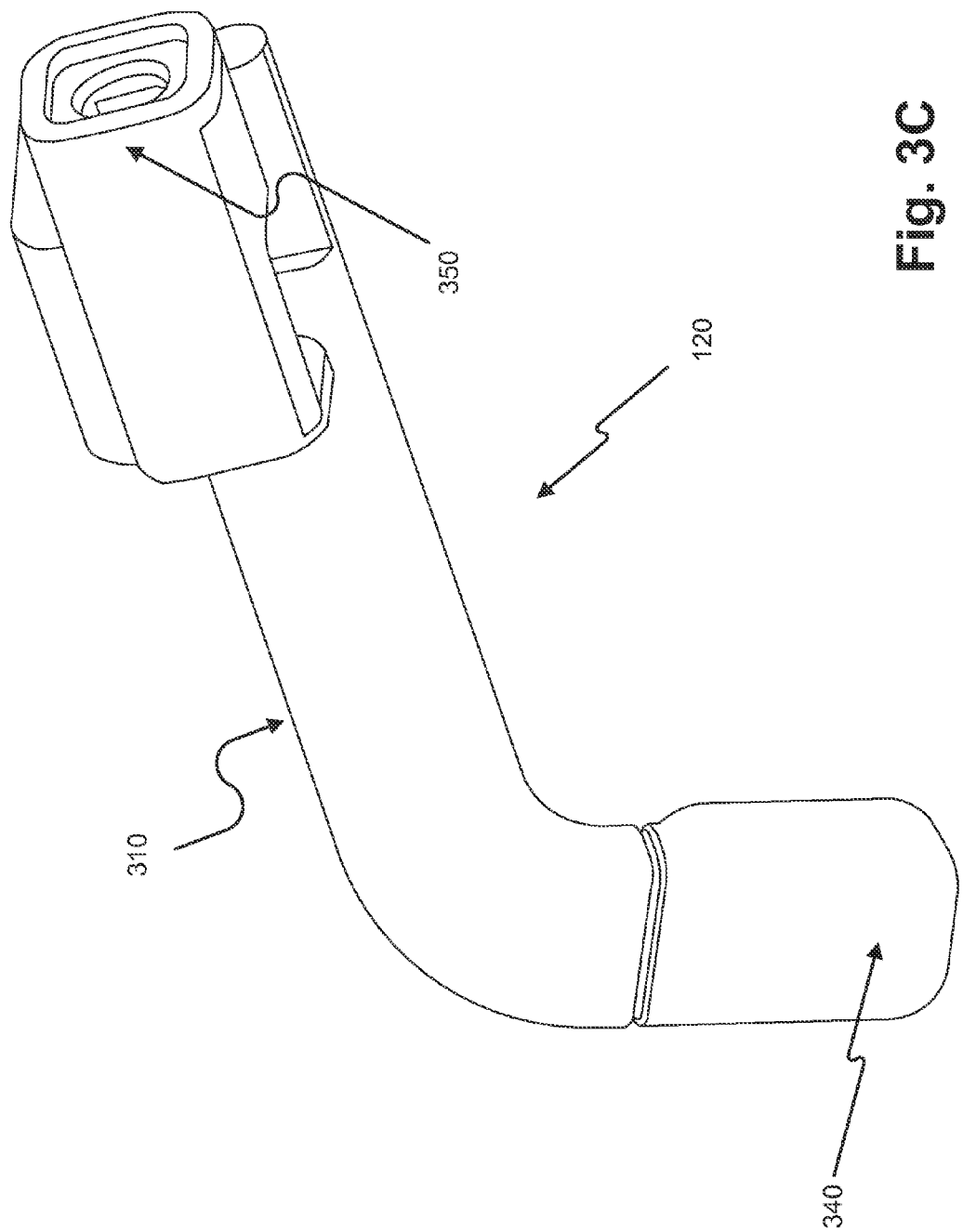

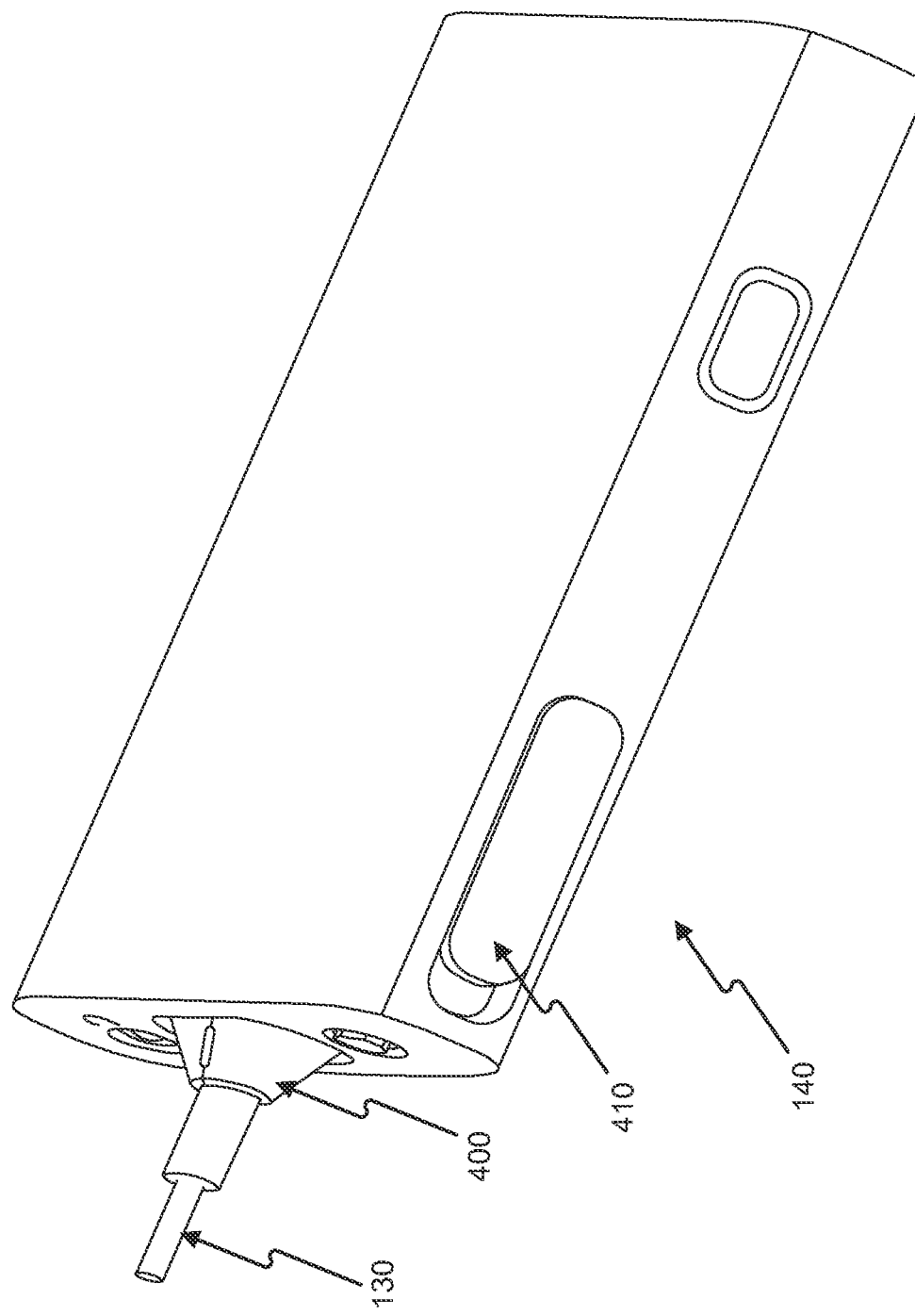

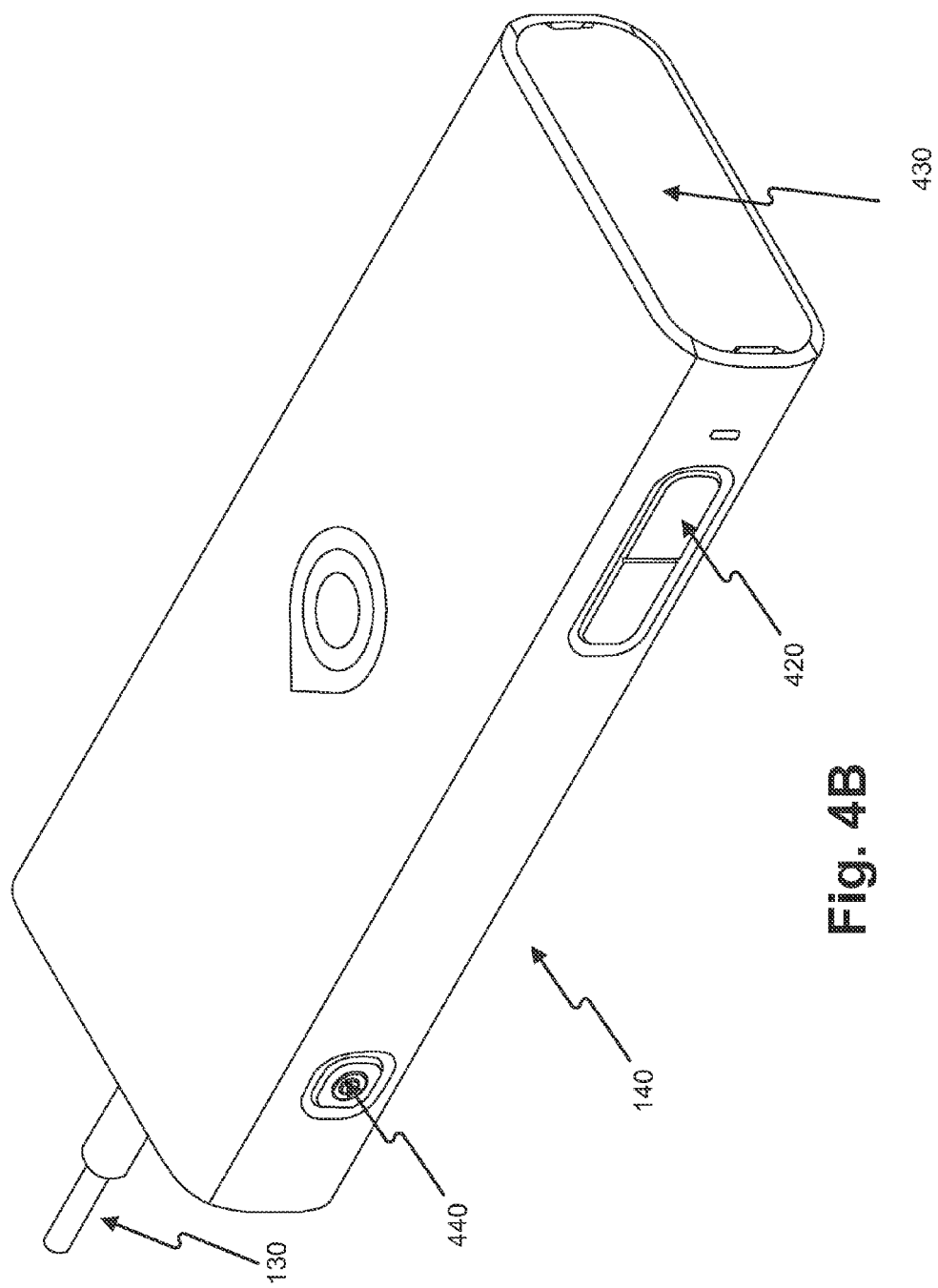

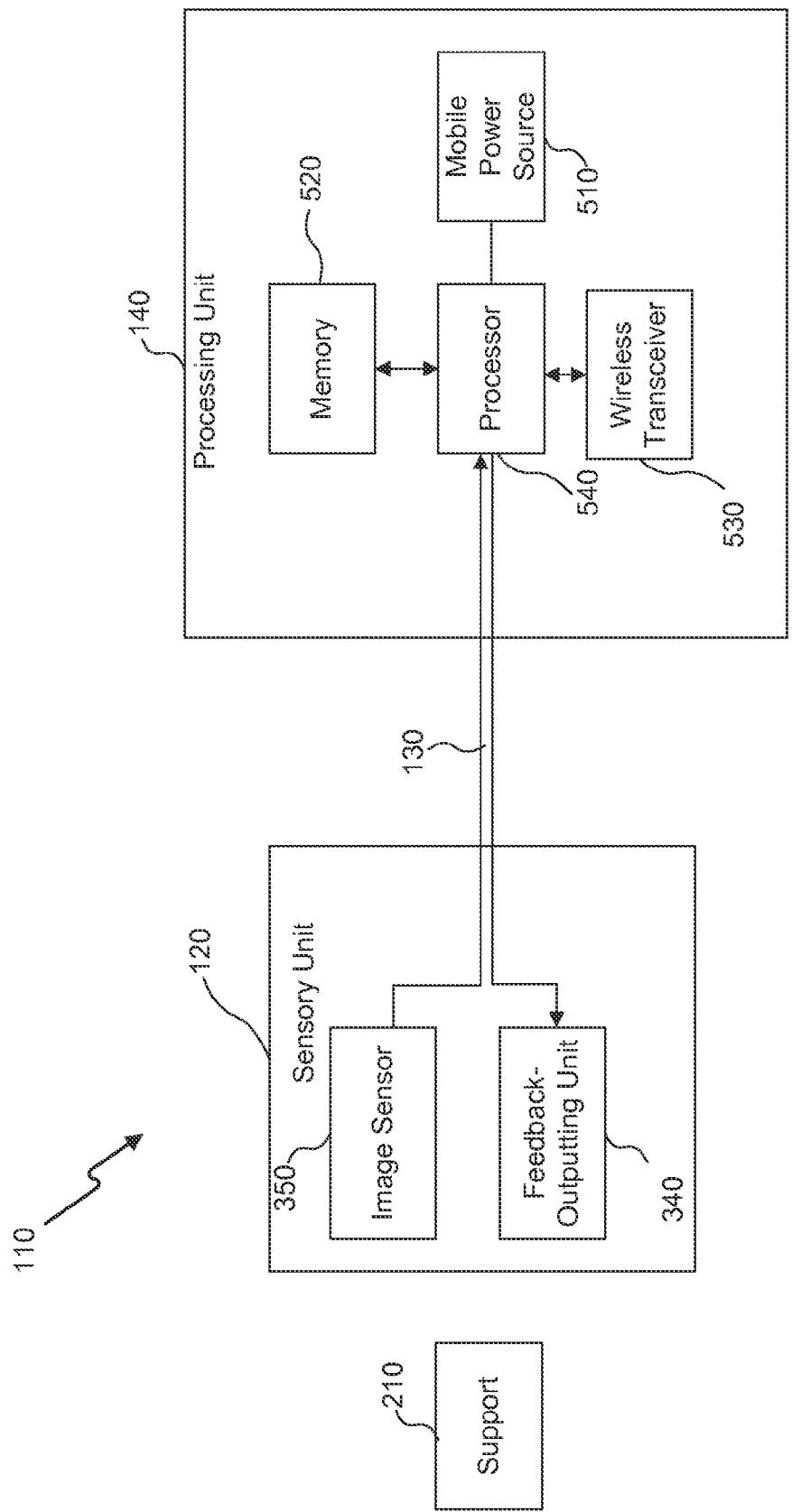

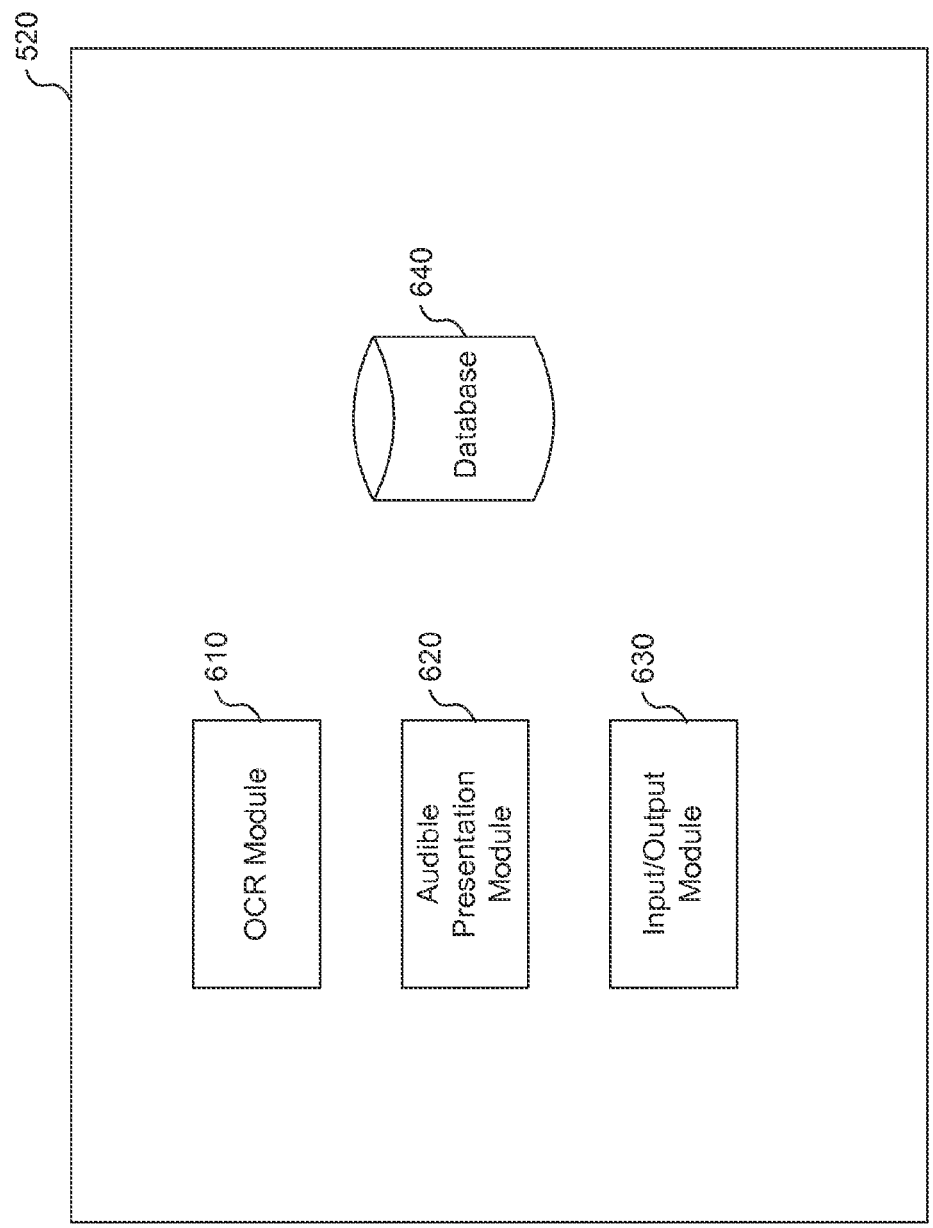

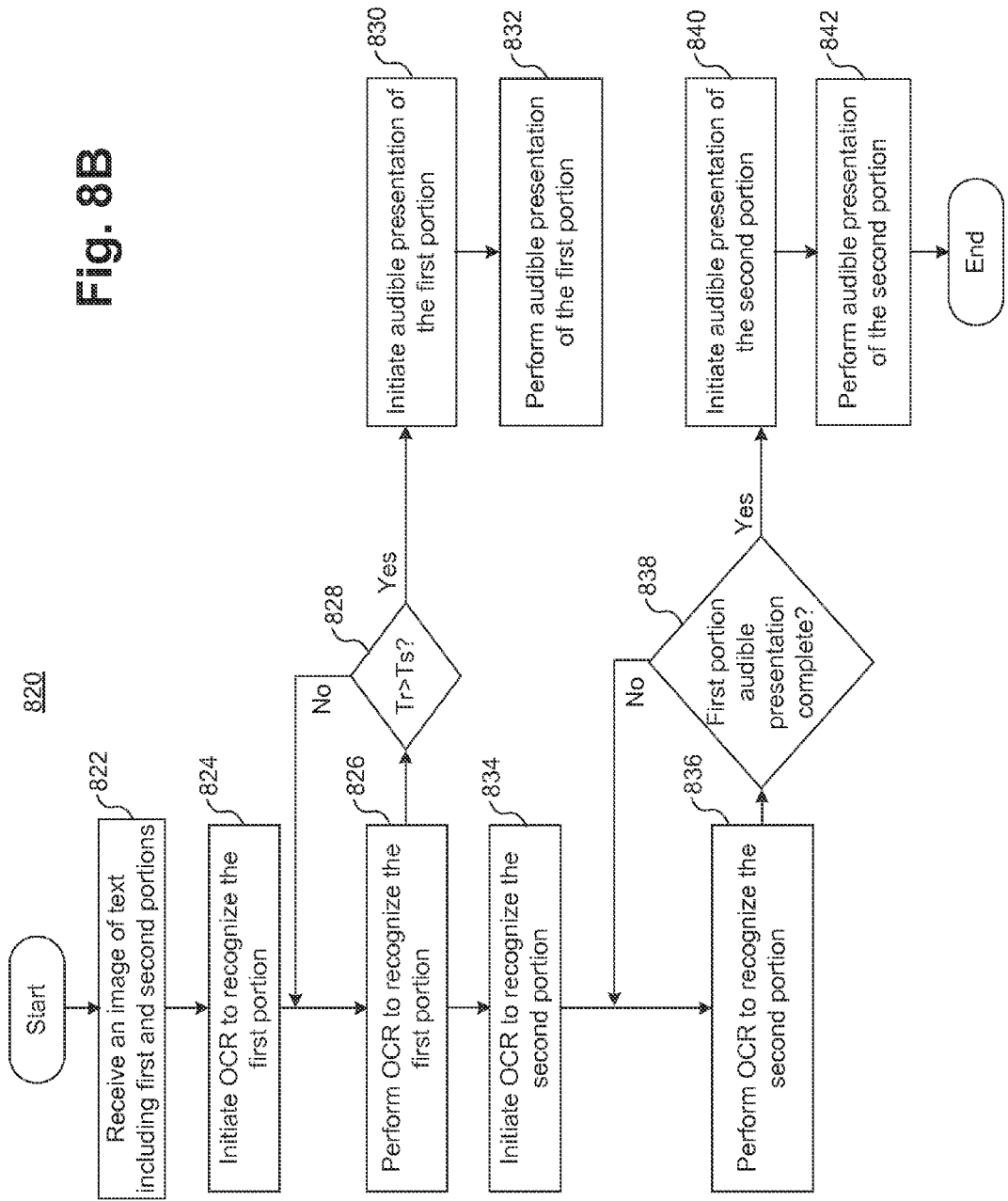

APPARATUS, METHOD, AND COMPUTER READABLE MEDIUM FOR EXPEDITED TEXT READING USING STAGED OCR TECHNIQUE

CROSS REFERENCE TO RELATED APPLICATIONS

This application claims the benefit of priority of U.S. Provisional Patent Application No. 61/799,649, filed on Mar. 15, 2013, and U.S. Provisional Patent Application No. 61/830,122, filed on Jun. 2, 2013, both of which are incorporated herein by reference in their entirety.

BACKGROUND

I. Technical Field

This disclosure generally relates to devices and methods for providing information to a user. More particularly, this disclosure relates to devices and methods for providing information to a user by processing images captured from the environment of the user.

II. Background Information

Visual acuity is an indication of the clarity or clearness of a person's vision that is commonly measured twenty feet from an object. When measuring visual acuity, the ability of a person to identify black symbols on a white background at twenty feet is compared to the ability of a person with normal eyesight. This comparison can be symbolized by a ratio. For example, a ratio of 20/70 vision means a person located at a distance of twenty feet can see what a person with normal vision can see at seventy feet. A person has low vision if he or she has a visual acuity between 20/70 and 20/200 in the better-seeing eye that cannot be corrected or improved with regular eyeglasses. The prevalence of low vision is about one in a hundred for people in their sixties and rapidly increases to one in five for people in their nineties. Low vision may also depend on the environment. For example, some individuals may be able to see only when there is ample light.

A person may have low vision (also known as visual impairment) for several reasons. Other than eye damage and failure of the brain to receive visual cues sent by the eyes, different medical conditions may cause visual impairment. Medical conditions that may cause visual impairment include Age-related Macular Degeneration (AMD), retinitis pigmentosa, cataract, and diabetic retinopathy.

AMD, which usually affects adults, is caused by damage to the retina that diminishes vision in the center of a person's visual field. The lifetime risk for developing AMD is strongly associated with certain genes. For example, the lifetime risk of developing AMD is 50% for people that have a relative with AMD, versus 12% for people that do not have relatives with AMD.

Retinitis pigmentosa is an inherited, degenerative eye disease that causes severe vision impairment and often blindness. The disease process begins with changes in pigment and damage to the small arteries and blood vessels that supply blood to the retina. There is no cure for retinitis pigmentosa and no known treatment can stop the progressive vision loss caused by the disease.

A cataract is a clouding of the lens inside the eye which leads to a decrease in vision. Over time, a yellow-brown pigment is deposited within the lens and obstructs light from passing and being focused onto the retina at the back of the eye. Biological aging is the most common cause of a cataract, but a wide variety of other risk factors (e.g., excessive tanning, diabetes, prolonged steroid use) can cause a cataract.

Diabetic retinopathy is a systemic disease that affects up to 80% of all patients who have had diabetes for ten years or more. Diabetic retinopathy causes microvascular damage to a blood-retinal barrier in the eye and makes the retinal blood vessels more permeable to fluids.

People with low vision experience difficulties due to lack of visual acuity, field-of-view, color perception, and other visual impairments. These difficulties affect many aspects of everyday life. Persons with low vision may use magnifying glasses to compensate for some aspects of low vision. For example, if the smallest letter a person with 20/100 vision can read is five times larger than the smallest letter that a person with 20/20 vision can read, then 5× magnification should make everything that is resolvable to the person with 20/20 vision resolvable to the person with low vision. However, magnifying glasses are expensive and cannot remedy all aspects of low vision. For example, a person with low vision who wears magnifying glasses may still have a difficult time recognizing details from a distance (e.g., people, signboards, traffic lights, etc.). Accordingly, there is a need for other technologies that can assist people who have low vision accomplish everyday activities.

SUMMARY

Embodiments consistent with the present disclosure provide devices and methods for providing information to a user by processing images captured from the environment of the user. The disclosed embodiments may assist persons who have low vision.

In accordance with a disclosed embodiment, a system is provided for accelerating machine reading of text. The system comprises at least one processor device. The at least one processor device is configured to receive at least one image of text to be audibly read. The text includes a first portion and a second portion. The at least one processor device is further configured to initiate optical character recognition to recognize the first portion. The at least one processor device is further configured to initiate an audible presentation of the first portion prior to initiating optical character recognition of the second portion. The at least one processor device is further configured to simultaneously perform optical character recognition to recognize the second portion of the text to be audibly read during presentation of at least part of the first portion. The at least one processor device is further configured to automatically cause the second portion of the text to be audibly presented immediately upon completion of the presentation of the first portion.

In accordance with another disclosed embodiment, a system is provided for processing text. The system comprises a memory and at least one processor device. The at least one processor device is configured to receive at least one image capturing an environment of a user. The at least one image includes text having a first portion and a second portion. The at least one processor device is further configured to initiate optical character recognition to recognize the first portion of the text and store in the memory a first plurality of words associated with the first portion. The at least one processor device is further configured to execute an action relative to the first plurality of words prior to initiating optical character recognition to recognize the second portion of the text. The at least one processor device is further configured to store in the memory a second plurality of words associated with the second portion and execute the action relative to the second plurality of words immediately upon completion of the action on the first plurality of words.

In accordance with yet another disclosed embodiment, a method is provided for accelerating machine reading of text. The method comprises receiving from a mobile image sensor at least one image of text to be audibly read. The text includes a first portion and a second portion. The method further comprises initiating optical character recognition to recognize the first portion. The method further comprises initiating an audible presentation of the first portion prior to initiating optical character recognition of the second portion. The method further comprises simultaneously performing optical character recognition to recognize the second portion of the text to be audibly read during presentation of at least part of the first portion. The method further comprises automatically causing the second portion of the text to be audibly presented immediately upon completion of the presentation of the first portion.

Consistent with other disclosed embodiments, non-transitory computer-readable storage media may store program instructions, which are executed by at least one processor device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate various disclosed embodiments. In the drawings:

FIG. 2C is a schematic illustration of the support shown in FIG. 2A mounted on a pair of glasses;

FIG. 3C is a schematic illustration of the sensory unit shown in FIG. 3A from a third viewpoint;

FIG. 4A is a schematic illustration of an example of a processing unit from a first viewpoint;

FIG. 4B is a schematic illustration of the processing unit shown in FIG. 4A from a second viewpoint;

FIG. 5A is a block diagram illustrating an example of the components of an apparatus for aiding persons who have low vision according to a first embodiment;

FIG. 6 is a block diagram illustrating an example of a memory storing software modules;

FIG. 8B is a flow chart of an exemplary process for accelerating machine reading of text, according to a second embodiment;

DETAILED DESCRIPTION

Figure 1:
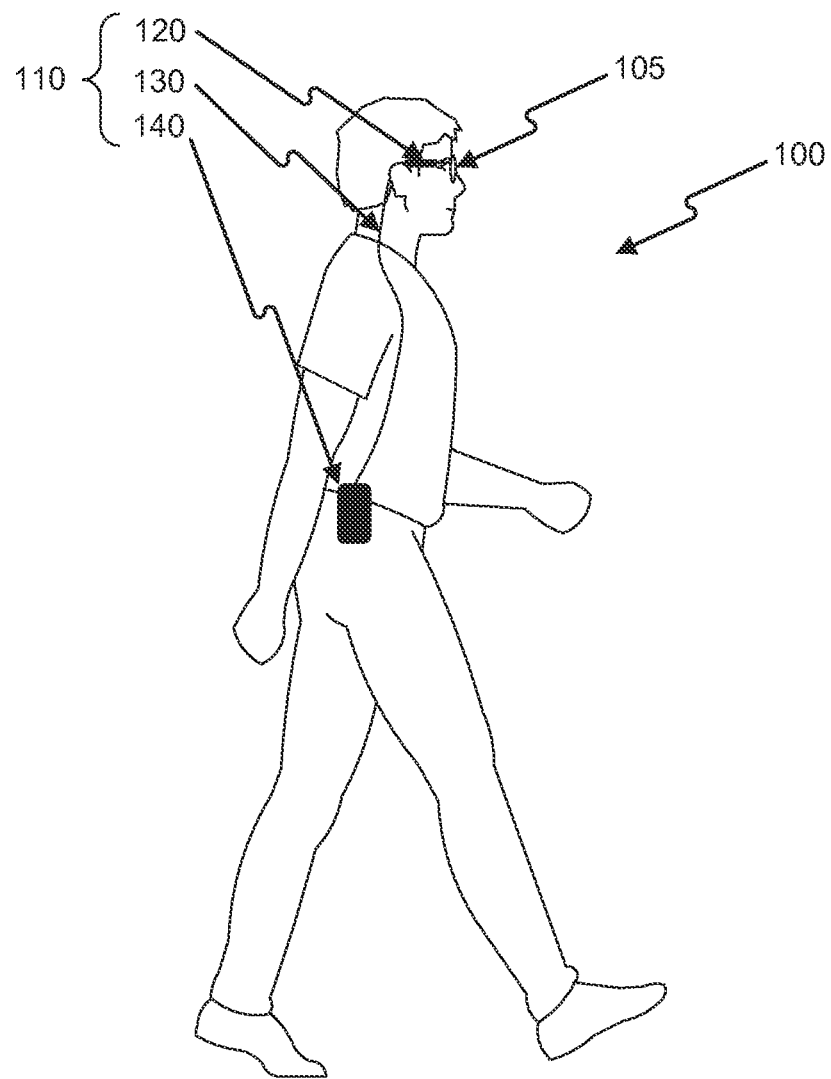
FIG. 1 is a schematic illustration of a user wearing an apparatus for aiding persons who have low vision.

The following detailed description refers to the accompanying drawings. Wherever possible, the same reference numbers are used in the drawings and the following description to refer to the same or similar parts. While several illustrative embodiments are described herein, modifications, adaptations, and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Disclosed embodiments provide devices and methods for assisting people who have low vision. One example of the disclosed embodiments is a device that includes a camera configured to capture real-time image data from the environment of the user. The device also includes a processing unit configured to process the real-time image data and provide real-time feedback to the user. The real-time feedback may include, for example, an output that audibly identifies individuals from a distance, reads signboards, and/or identifies the state of a traffic light.

FIG. 1 illustrates a user 100 wearing an apparatus 110 connected to glasses 105, consistent with a disclosed embodiment. Apparatus 110 may provide functionality for aiding user 100 with various daily activities that are otherwise difficult for user 100 to accomplish due to low vision. Glasses 105 may be prescription glasses, magnifying glasses, non-prescription glasses, safety glasses, sunglasses, etc.

As shown in FIG. 1, apparatus 110 includes a sensory unit 120 and a processing unit 140. Sensory unit 120 may be connected to a support (not shown in FIG. 1) that is mounted on glasses 105. In addition, sensory unit 120 may include an image sensor (not shown in FIG. 1) for capturing real-time image data of the field-of-view of user 100. The term "image data" includes any form of data retrieved from optical signals in the near-infrared, infrared, visible, and ultraviolet spectrums. The image data may be used to form video clips and/or photographs.

Processing unit 140 may communicate wirelessly or via a wire 130 connected to sensory unit 120. In some embodiments, processing unit 140 may produce an output of audible feedback to user 100 (e.g., using a speaker or a bone conduction headphone).

Apparatus 110 is one example of a device capable of implementing the functionality of the disclosed embodiments. Other devices capable of implementing the disclosed embodiments include, for example, a mobile computer with a camera (e.g., a smartphone, a smartwatch, a tablet, etc.) or a clip-on-camera configured to communicate with a processing unit (e.g., a smartphone or a dedicated processing unit, which can be carried in a pocket). A person skilled in the art will appreciate that different types of devices and arrangements of devices may implement the functionality of the disclosed embodiments.

Figure 2A:
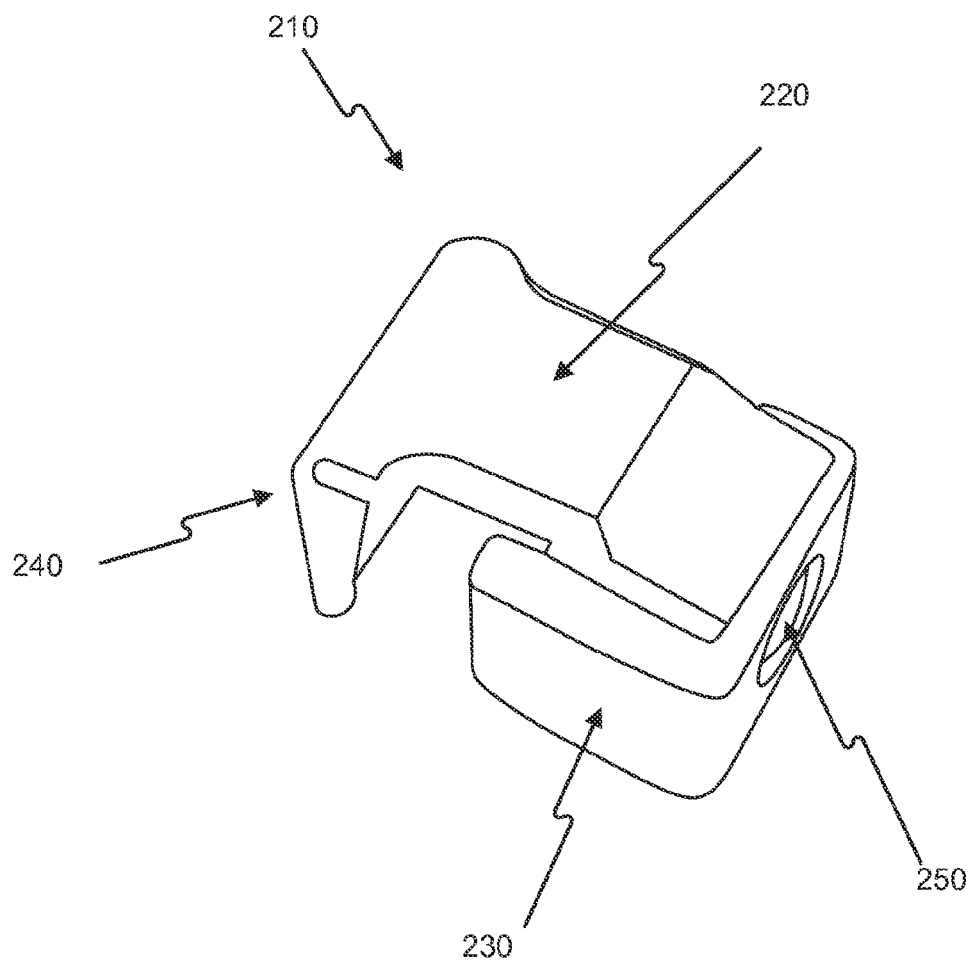
FIG. 2A is a schematic illustration of an example of a support from a first viewpoint.

FIG. 2A is a schematic illustration of an example of a support 210. As discussed in connection with FIG. 1, support 210 may be mounted on glasses 105 and connect to sensory unit 120. The term "support" includes any device or structure that enables detaching and reattaching of a device including a camera to a pair of glasses or to another object (e.g., a helmet). Support 210 may be made from plastic (e.g., polycarbonate), metal (e.g., aluminum), or a combination of plastic and metal (e.g., carbon fiber graphite). Support 210 may be mounted on glasses 105 using screws, bolts, snaps, or any fastening means used in the art.

As shown in FIG. 2A, support 210 includes a base 230 connected to a clamp 240. A bridge 220 connects base 230 with clamp 240. Base 230 and clamp 240 enable sensory unit 120 to easily attach to and detach from support 210. In one embodiment, base 230 may include an internally threaded member 250 for cooperating with a screw (not shown in FIG. 2A) to mount support 210 on glasses 105.

Figure 2B:
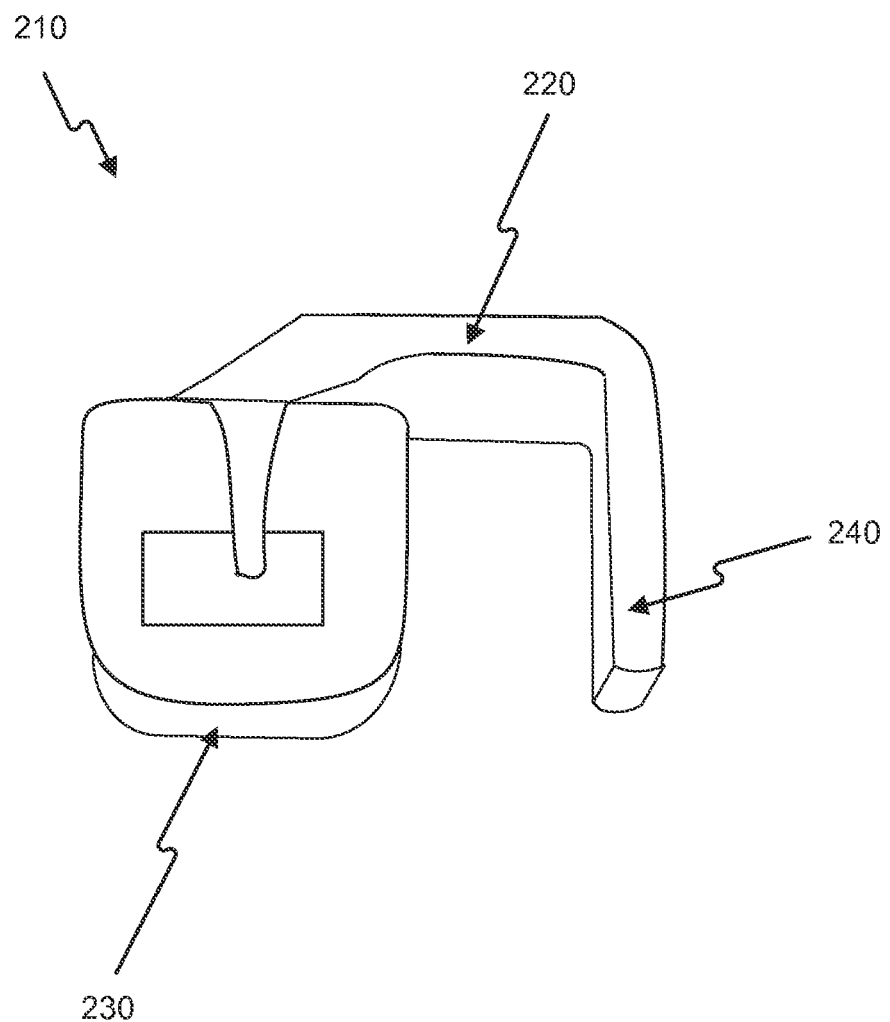
FIG. 2B is a schematic illustration of the support shown in FIG. 2A from a second viewpoint.

FIG. 2B illustrates support 210 from a second viewpoint. The viewpoint shown in FIG. 2B is from a side orientation of support 210.

FIG. 2C illustrates support 210 mounted on glasses 105. Support 210 may be configured for mounting on any kind of glasses (e.g., eyeglasses, sunglasses, 3D glasses, safety glasses, etc.). As shown in FIG. 2C, sensory unit 120 is not attached to support 210 and, accordingly, support 210 may be sold separately from apparatus 110. This arrangement makes apparatus 110 compatible with a variety of glasses. For example, some users may have several pairs of glasses and may wish to mount a support on each pair of glasses.

In other embodiments, support 210 may be an integral part of a pair of glasses, or sold and installed by an optometrist. For example, support 210 may be configured for mounting on the arms of glasses 105 near the frame front, but before the hinge. Alternatively, support 210 may be configured for mounting on the bridge of glasses 105.

Figure 2D:
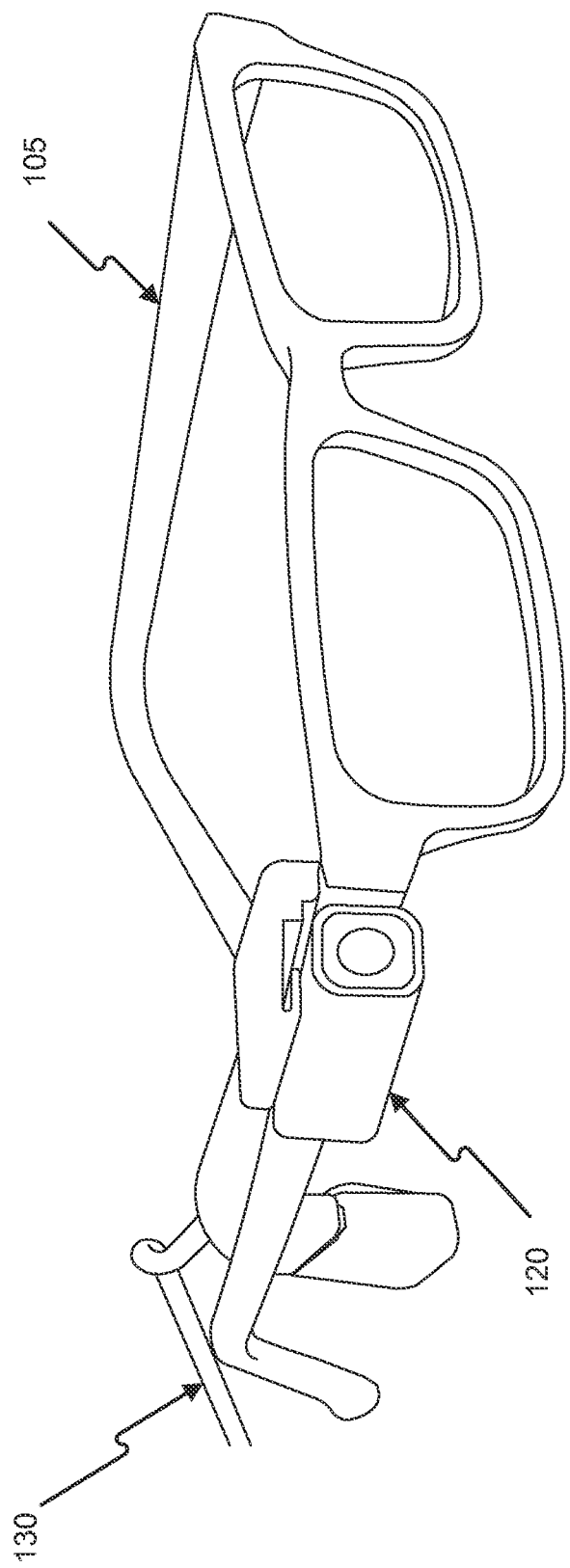
FIG. 2D is a schematic illustration of a sensory unit attached to the support that is mounted on the pair of glasses shown in FIG. 2C.

FIG. 2D illustrates sensory unit 120 attached to support 210 (not visible in FIG. 2D), and support 210 mounted on glasses 105. In some embodiments, support 210 may include a quick release mechanism for disengaging and reengaging sensory unit 120. For example, support 210 and sensory unit 120 may include magnetic elements. As an alternative example, support 210 may include a male latch member and sensory unit 120 may include a female receptacle.

When sensory unit 120 is attached (or reattached) to support 210, the field-of-view of a camera associated with sensory unit 120 may be substantially identical to the field-of-view of user 100. Accordingly, in some embodiments, after support 210 is attached to sensory unit 120, directional calibration of sensory unit 120 may not be required because sensory unit 120 aligns with the field-of-view of user 100.

In other embodiments, support 210 may include an adjustment component (not shown in FIG. 2D) to enable calibration of the aiming direction of sensory unit 120 in a substantially set position that is customized to user 100 wearing glasses 105. For example, the adjustment component may include an adjustable hinge to enable vertical and horizontal alignment of the aiming direction of sensory unit 120. Adjusting the alignment of sensory unit 120 may assist users who have a unique and individual visual impairment. The adjustment may be internal or external to sensory unit 120.

Figure 2E:
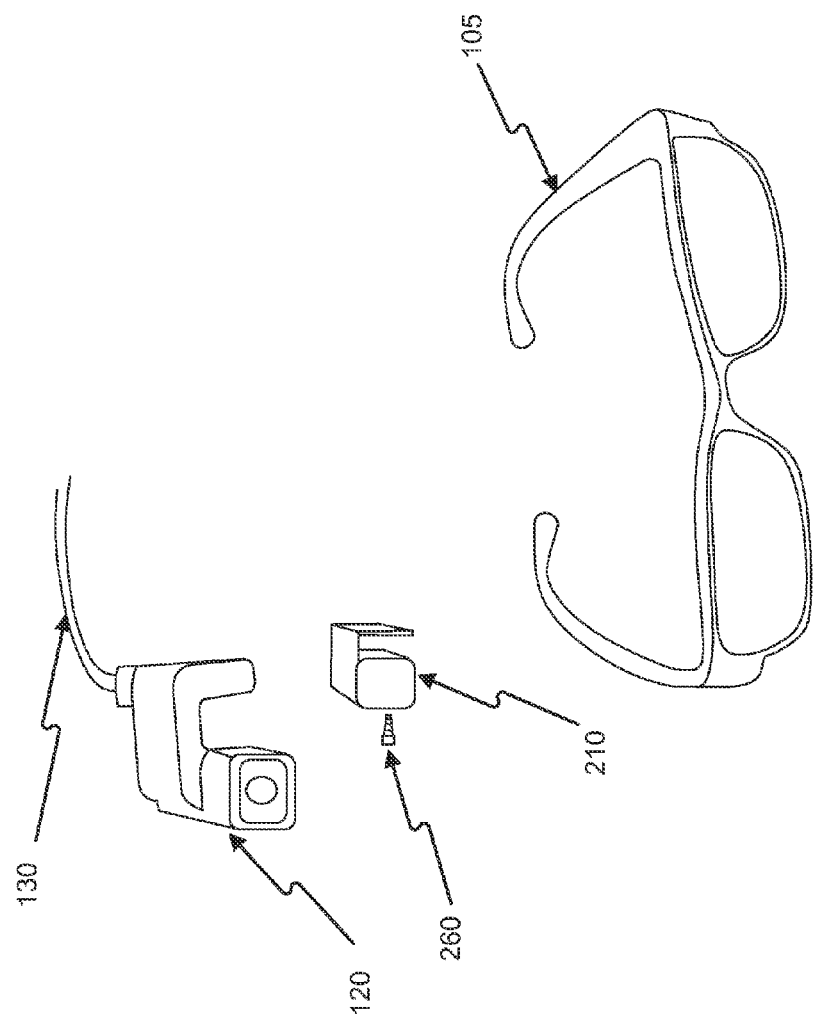
FIG. 2E is an exploded view of FIG. 2D.

FIG. 2E is an exploded view of the components shown in FIG. 2D. Sensory unit 120 may be attached to glasses 105 in the following way. Initially, support 210 may be mounted on glasses 105 using screw 260. Next, screw 260 may be inserted into internally threaded member 250 (not shown in FIG. 2E) in the side of support 210. Sensory unit 120 may then be clipped on support 210 such that it is aligned with the field-of-view of user 100.

Figure 3A:
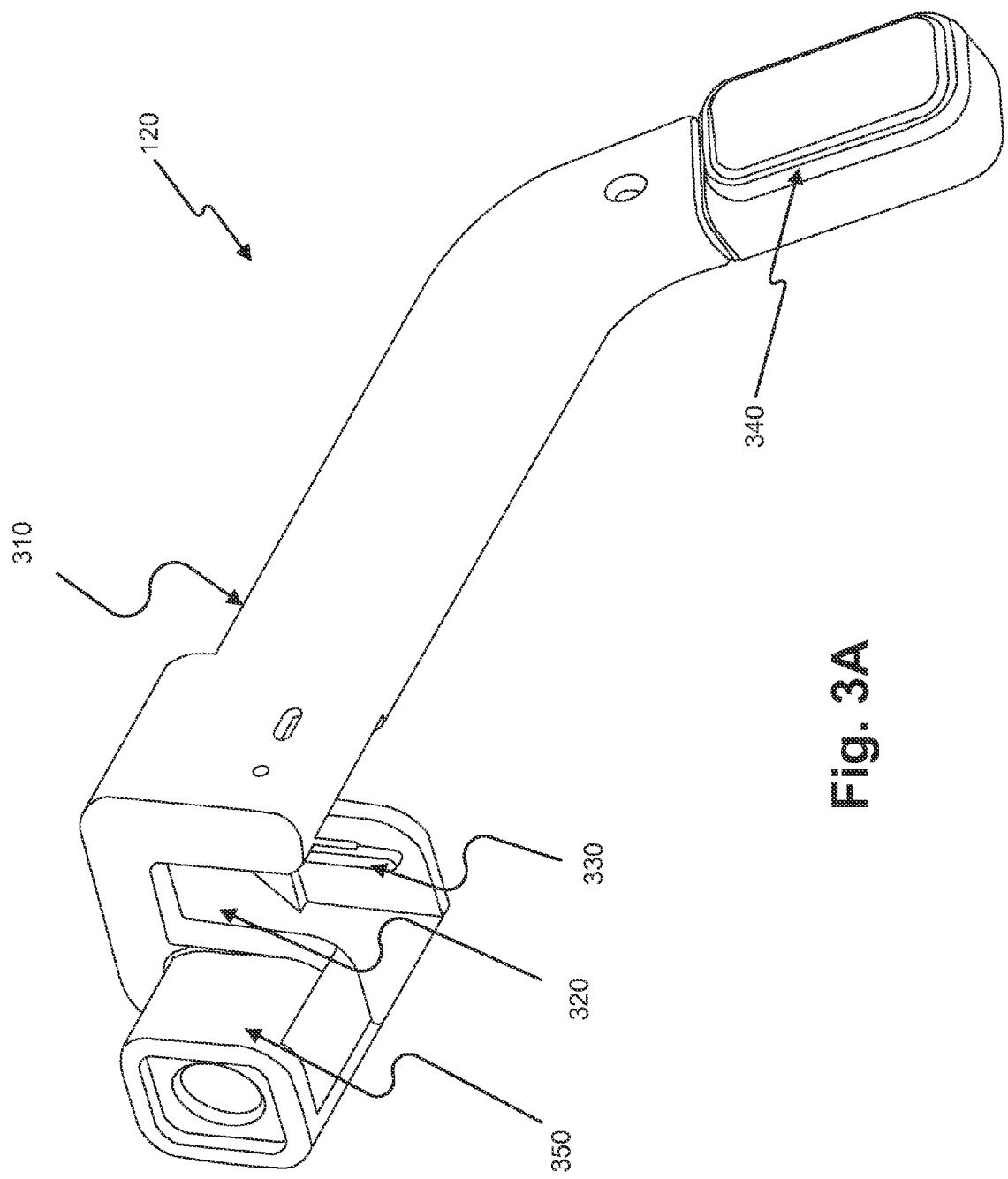
FIG. 3A is a schematic illustration of an example of a sensory unit from a first viewpoint.

FIG. 3A is a schematic illustration of sensory unit 120 from a first viewpoint. As shown in FIG. 3A, sensory unit 120 includes a feedback-outputting unit 340 and an image sensor 350.

Sensory unit 120 is configured to cooperate with support 210 using clip 330 and groove 320, which fits the dimensions of support 210. The term "sensory unit" refers to any electronic device configured to capture real-time images and provide a non-visual output. Furthermore, as discussed above, sensory unit 120 includes feedback-outputting unit 340. The term "feedback-outputting unit" includes any device configured to provide information to a user.

In some embodiments, feedback-outputting unit 340 may be configured to be used by blind persons and persons with low vision. Accordingly, feedback-outputting unit 340 may be configured to output nonvisual feedback. The term "feedback" refers to any output or information provided in response to processing at least one image in an environment. For example, feedback may include a descriptor of a branded product, an audible tone, a tactile response, and/or information previously recorded by user 100. Furthermore, feedback-outputting unit 340 may comprise appropriate components for outputting acoustical and tactile feedback that people with low vision can interpret. For example, feedback-outputting unit 340 may comprise audio headphones, a speaker, a bone conduction headphone, interfaces that provide tactile cues, vibrotactile stimulators, etc.

As discussed above, sensory unit 120 includes image sensor 350. The term "image sensor" refers to a device capable of detecting and converting optical signals in the near-infrared, infrared, visible, and ultraviolet spectrums into electrical signals. The electric signals may be used to form an image based on the detected signal. For example, image sensor 350 may be part of a camera. In some embodiments, when sensory unit 120 is attached to support 210, image sensor 350 may acquire a set aiming direction without the need for directional calibration. The set aiming direction of image sensor 350 may substantially coincide with the field-of-view of user 100 wearing glasses 105. For example, a camera associated with image sensor 350 may be installed within sensory unit 120 in a predetermined angle in a position facing slightly downwards (e.g., 5-15 degrees from the horizon). Accordingly, the set aiming direction of image sensor 350 may match the field-of-view of user 100.

As shown in FIG. 3A, feedback-outputting unit 340 and image sensor 350 are included in a housing 310. The term "housing" refers to any structure that at least partially covers, protects, or encloses a sensory unit. The housing may be made from one or more different materials (e.g., plastic or aluminum). In one embodiment, housing 310 may be designed to engage with a specific pair of glasses having a specific support (e.g., support 210). In an alternative embodiment, housing 310 may be designed to engage more than one pair of glasses, each having a support (e.g., support 210) mounted thereon. Housing 310 may include a connector for receiving power from an external mobile-power-source or an internal mobile-power-source, and for providing an electrical connection to image sensor 350.

Figure 3B:
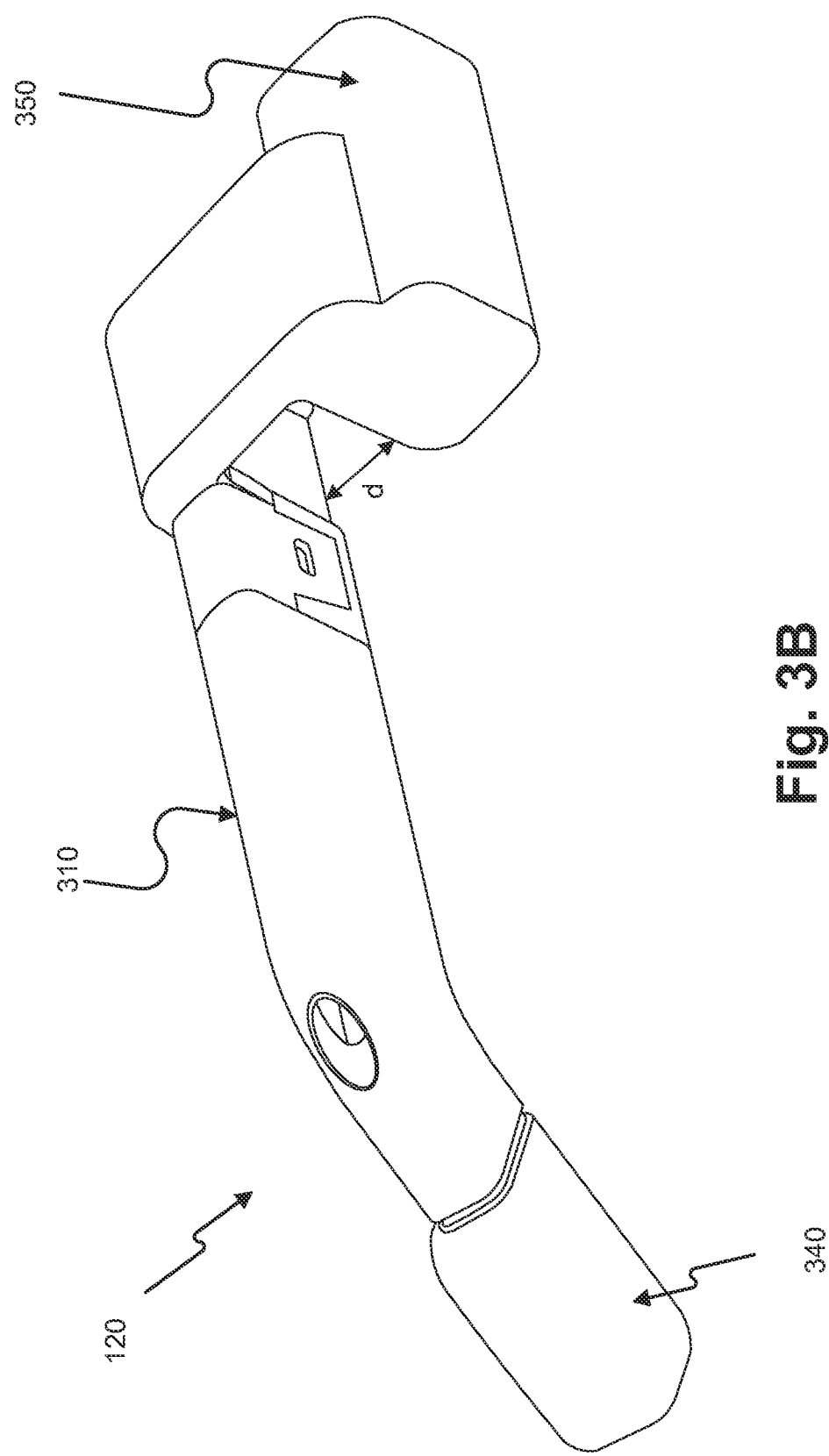
FIG. 3B is a schematic illustration of the sensory unit shown in FIG. 3A from a second viewpoint.

FIG. 3B is a schematic illustration of sensory unit 120 from a second viewpoint. As shown in FIG. 3B, housing 310 includes a U-shaped element. An inner distance "d" between each side of the U-shaped element is larger than the width of the arm of glasses 105. Additionally, the inner distance "d" between each side of the U-shaped element is substantially equal to a width of support 210. The inner distance "d" between each side of the U-shaped element may allow user 100 to easily attach housing 310 to support 210, which may be mounted on glasses 105. As illustrated in FIG. 3B, image sensor 350 is located on one side of the U-shaped element and feedback-outputting unit 340 is located on another side of the U-shaped element.

FIG. 3C is a schematic illustration of sensory unit 120 from a third viewpoint. The viewpoint shown in FIG. 3C is from a side orientation of sensory unit 120 and shows the side of the U-shaped element that includes image sensor 350.

Figure 3D:
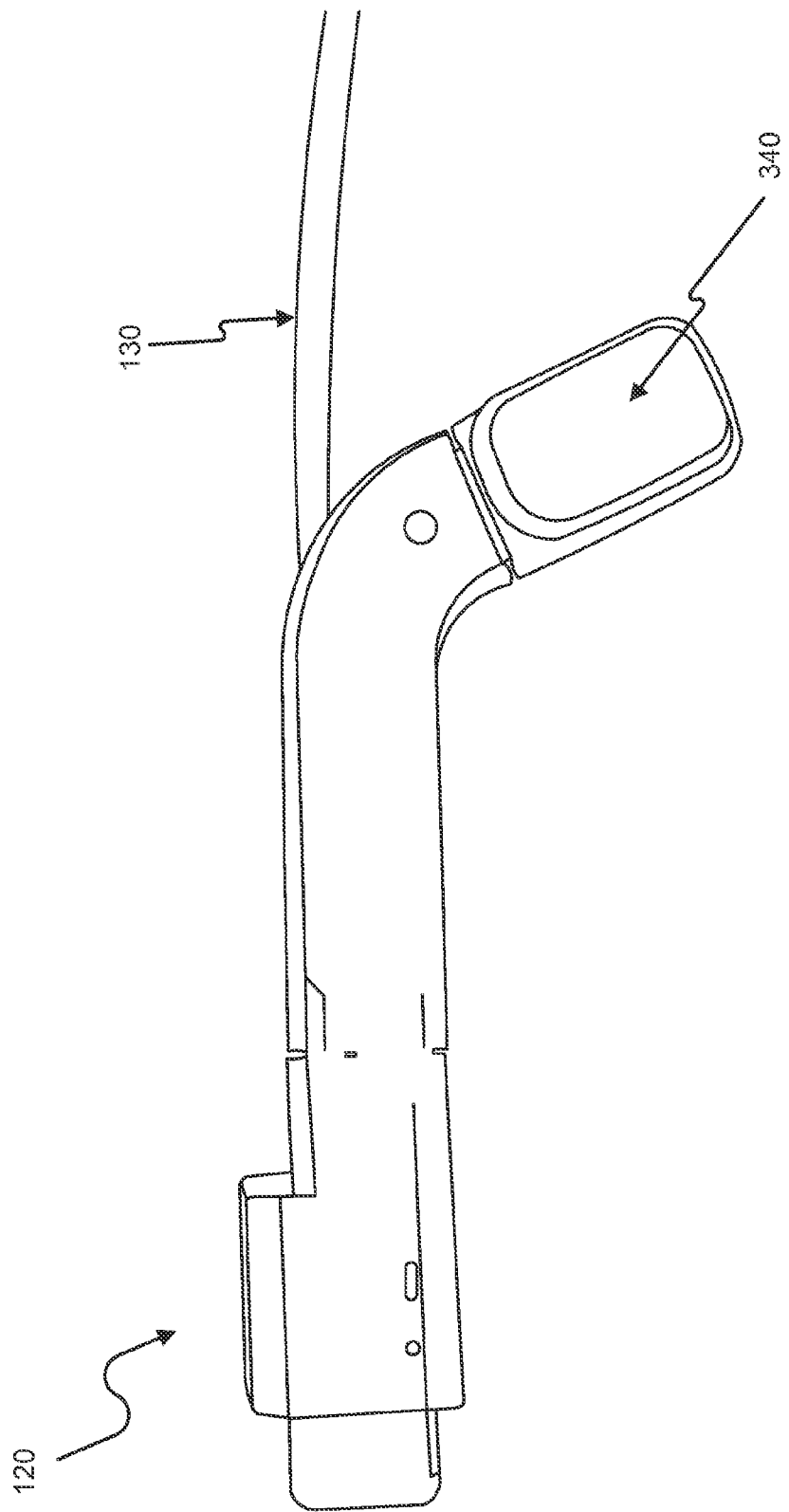
FIG. 3D is a schematic illustration of the sensory unit shown in FIG. 3A from a fourth viewpoint.

FIG. 3D is a schematic illustration of sensory unit 120 from a fourth viewpoint. The viewpoint shown in FIG. 3D is from an opposite side of the orientation shown in FIG. 3C. FIG. 3D shows the side of the U-shaped element that includes feedback-outputting unit 340.

Figure 3E:
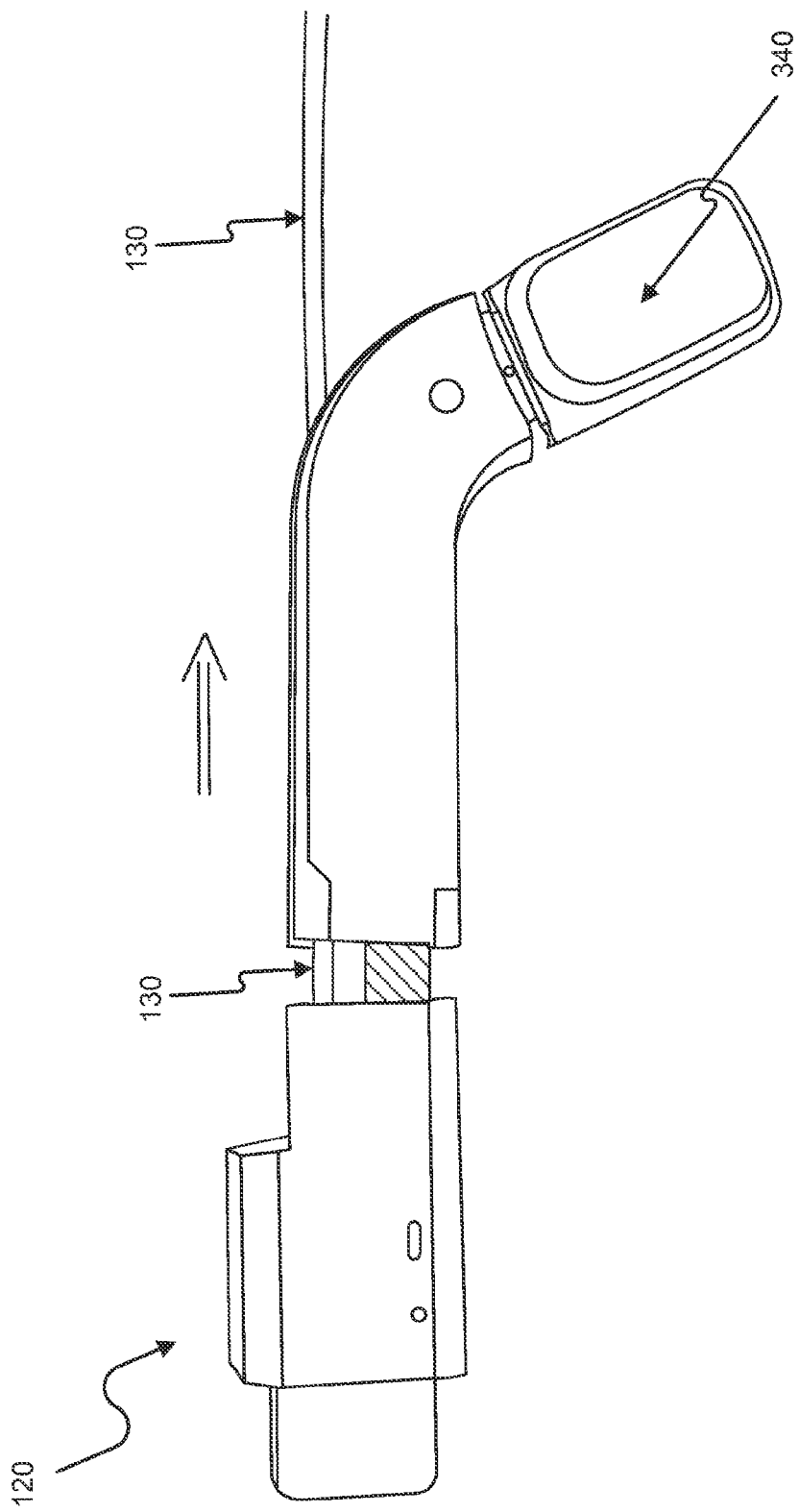
FIG. 3E is a schematic illustration of the sensory unit shown in FIG. 3A in an extended position.

FIG. 3E is a schematic illustration of the sensory unit shown in FIG. 3A in an extended position. As shown in FIG. 3E, a portion of sensory unit 120 is extendable and wire 130 may pass through a channel of sensory unit 120. This arrangement may allow a user to adjust the length and the angle of sensory unit 120 without interfering with the operation of apparatus 110.

User 100 may adjust the U-shaped element of sensory unit 120 so that feedback-outputting unit 340 is positioned adjacent to the user's ear or the user's temple. Accordingly, sensory unit 120 may be adjusted for use with different users who may have different head sizes. Alternatively, a portion of sensory unit 120 may be flexible such that the angle of feedback-outputting unit 340 is relative to the user's ear or the user's temple.

FIG. 4A is a schematic illustration of processing unit 140. As shown in FIG. 4A, processing unit 140 has a rectangular shape, which easily fits in a pocket of user 100. Processing unit 140 includes a connector 400 for connecting wire 130 to processing unit 140. Wire 130 may be used to transmit power from processing unit 140 to sensory unit 120, and data to and from processing unit 140 to sensory unit 120. Alternatively, wire 130 may comprise multiple wires (e.g., a wire dedicated to power transmission and a wire dedicated to data transmission).

Processing unit 140 includes a function button 410 for enabling user 100 to provide input to apparatus 110. Function button 410 may accept different types of tactile input (e.g., a tap, a click, a double-click, a long press, a right-to-left slide, a left-to-right slide). In some embodiments, each type of input may be associated with a different action. For example, a tap may be associated with the function of confirming an action, while a right-to-left slide may be associated with the function of repeating the last output.

FIG. 4B is a schematic illustration of processing unit 140 from a second viewpoint. As shown in FIG. 4B, processing unit 140 includes a volume switch 420, a battery pack compartment 430, and a power port 440. In one embodiment, user 100 may charge apparatus 110 using a charger connectable to power port 440. Alternatively, user 100 may replace a battery pack (not shown) stored in battery pack compartment 430.

FIG. 5A is a block diagram illustrating the components of apparatus 110 according to a first embodiment. Specifically, FIG. 5A depicts an embodiment in which apparatus 110 comprises sensory unit 120 and processing unit 140, as discussed in connection with, for example, FIG. 1. Furthermore, sensory unit 120 may be physically coupled to support 210.

As shown in FIG. 5A, sensory unit 120 includes feedback-outputting unit 340 and image sensor 350. Although one image sensor is depicted in FIG. 5A, sensory unit 120 may include a plurality of image sensors (e.g., two image sensors). For example, in an arrangement with more than one image sensor, each of the image sensors may be face a different direction or be associated with a different camera (e.g., a wide angle camera, a narrow angle camera, an IR camera, etc.). In other embodiments (not shown in the figure) sensory unit 120 may also include buttons and other sensors such as a microphone and inertial measurements devices.

As further shown in FIG. 5A, sensory unit 120 is connected to processing unit 140 via wire 130. Processing unit 140 includes a mobile power source 510, a memory 520, a wireless transceiver 530, and a processor 540.

Processor 540 may constitute any physical device having an electric circuit that performs a logic operation on input or inputs. For example, processor 540 may include one or more integrated circuits, microchips, microcontrollers, microprocessors, all or part of a central processing unit (CPU), graphics processing unit (GPU), digital signal processor (DSP), field-programmable gate array (FPGA), or other circuits suitable for executing instructions or performing logic operations. The instructions executed by processor 540 may, for example, be pre-loaded into a memory integrated with or embedded into processor 540 or may be stored in a separate memory (e.g., memory 520). Memory 520 may comprise a Random Access Memory (RAM), a Read-Only Memory (ROM), a hard disk, an optical disk, a magnetic medium, a flash memory, other permanent, fixed, or volatile memory, or any other mechanism capable of storing instructions.

Although one processor is shown in FIG. 5A, processing unit 140 may include more than one processor. Each processor may have a similar construction or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

In some embodiments, processor 540 may change the aiming direction of image sensor 350 using image data provided from image sensor 350. For example, processor 540 may recognize that a user is reading a book and determine that the aiming direction of image sensor 350 is offset from the text. That is, because the words in the beginning of each line of text are not fully in view, processor 540 may determine that image sensor 350 is tilted down and to the right. Responsive thereto, processor 540 may adjust the aiming direction of image sensor 350.

Processor 540 may access memory 520. Memory 520 may be configured to store information specific to user 100. For example, data for image representations of known individuals, favorite products, personal items, etc., may be stored in memory 520. In one embodiment, user 100 may have more than one pair of glasses, with each pair of glasses having support 210 mounted thereon. Accordingly, memory 520 may store information (e.g., personal settings) associated with each pair of glasses. For example, when a user wears his sunglasses may have different preferences than when the user wears reading glasses.

As shown in FIG. 5A, processing unit 140 includes mobile power source 510. Mobile power source 510 may be configured to power processing unit 140 and/or sensory unit 120. The term "mobile power source" includes any device capable of providing electrical power, which can be easily carried by a hand (e.g., the total weight of mobile power source 510 may be less than a pound). Thus, the mobility of the power source enables user 100 to use apparatus 110 in a variety of situations. For example, mobile power source 510 may include one or more batteries (e.g., nickel-cadmium batteries, nickel-metal hydride batteries, and lithium-ion batteries) or any other type of electrical power supply. In some embodiments, mobile power source 510 may be rechargeable and contained within a casing that holds processing unit 140. In other embodiments, mobile power source 510 may include one or more energy harvesting devices for converting ambient energy into electrical energy (e.g., portable solar power units, human vibration units, etc.).

Apparatus 110 may operate in a low-power-consumption mode and in a processing-power-consumption mode. For example, mobile power source 510 can produce five hours of processing-power-consumption mode and fifteen hours of low-power-consumption mode. Accordingly, different power consumption modes may allow mobile power source 510 to produce sufficient power for powering processing unit 140 for various time periods (e.g., more than two hours, more than four hours, more than ten hours, etc.).

Mobile power source 510 may power one or more wireless transceivers (e.g., wireless transceiver 530 in FIG. 5A). The term "wireless transceiver" refers to any device configured to exchange transmissions over an air interface by use of radio frequency, infrared frequency, magnetic field, or electric field. Wireless transceiver 530 may use any known standard to transmit and/or receive data (e.g., Wi-Fi, Bluetooth®, Bluetooth Smart, 802.15.4, or ZigBee). In some embodiments, wireless transceiver 530 may transmit data (e.g., raw image data or audio data) from image sensor 350 to processing unit 140, or wireless transceiver 530 may transmit data from processing unit 140 to feedback-outputting unit 340.

In another embodiment, wireless transceiver 530 may communicate with a different device (e.g., a hearing aid, the user's smartphone, or any wirelessly controlled device) in the environment of user 100. For example, wireless transceiver 530 may communicate with an elevator using a Bluetooth® controller. In such an arrangement, apparatus 110 may recognize that user 100 is approaching an elevator and call the elevator, thereby minimizing wait time. In another example, wireless transceiver 530 may communicate with a smart TV. In such an arrangement, apparatus 110 may recognize that user 100 is watching television and identify specific hand movements as commands for the smart TV (e.g., switching channels). In yet another example, wireless transceiver 530 may communicate with a virtual cane. A virtual cane is any device that uses a laser beam or ultrasound waves to determine the distance from user 100 to an object.

Figure 5B:
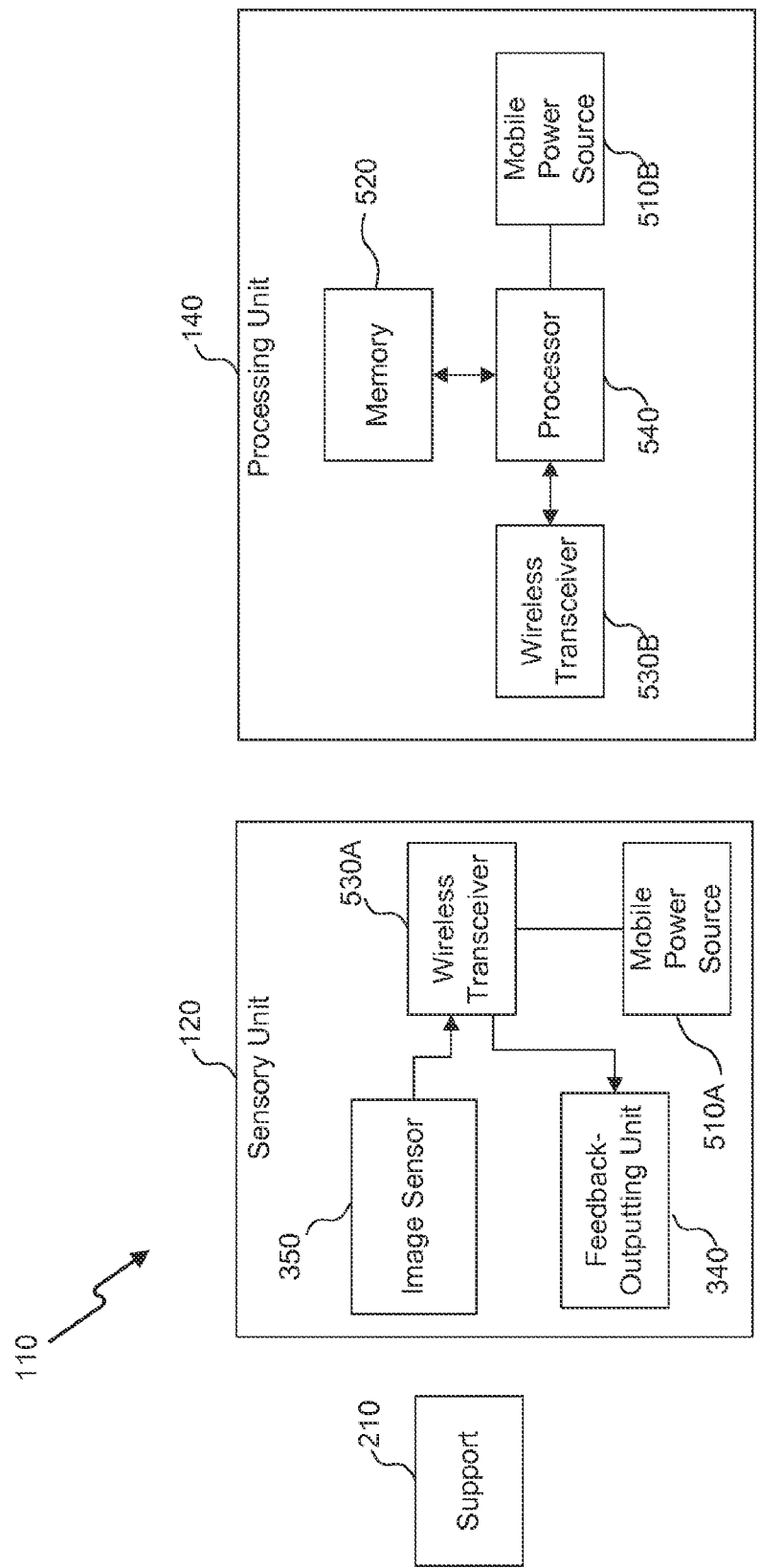
FIG. 5B is a block diagram illustrating an example of the components of an apparatus for aiding persons who have low vision according to a second embodiment.

FIG. 5B is a block diagram illustrating the components of apparatus 110 according to a second embodiment. In FIG. 5B, similar to the arrangement shown in FIG. 5A, support 210 is used to couple sensory unit 120 to a pair of glasses. However, in the embodiment shown in FIG. 5B, sensory unit 120 and processing unit 140 communicate wirelessly. For example, wireless transceiver 530A can transmit image data to processing unit 140 and receive information to be outputted via feedback-outputting unit 340.

In this embodiment, sensory unit 120 includes feedback-outputting unit 340, mobile power source 510A, wireless transceiver 530A, and image sensor 350. Mobile power source 510A is contained within sensory unit 120. As further shown in FIG. 5B, processing unit 140 includes wireless transceiver 530B, processor 540, mobile power source 510B, and memory 520.

Figure 5C:
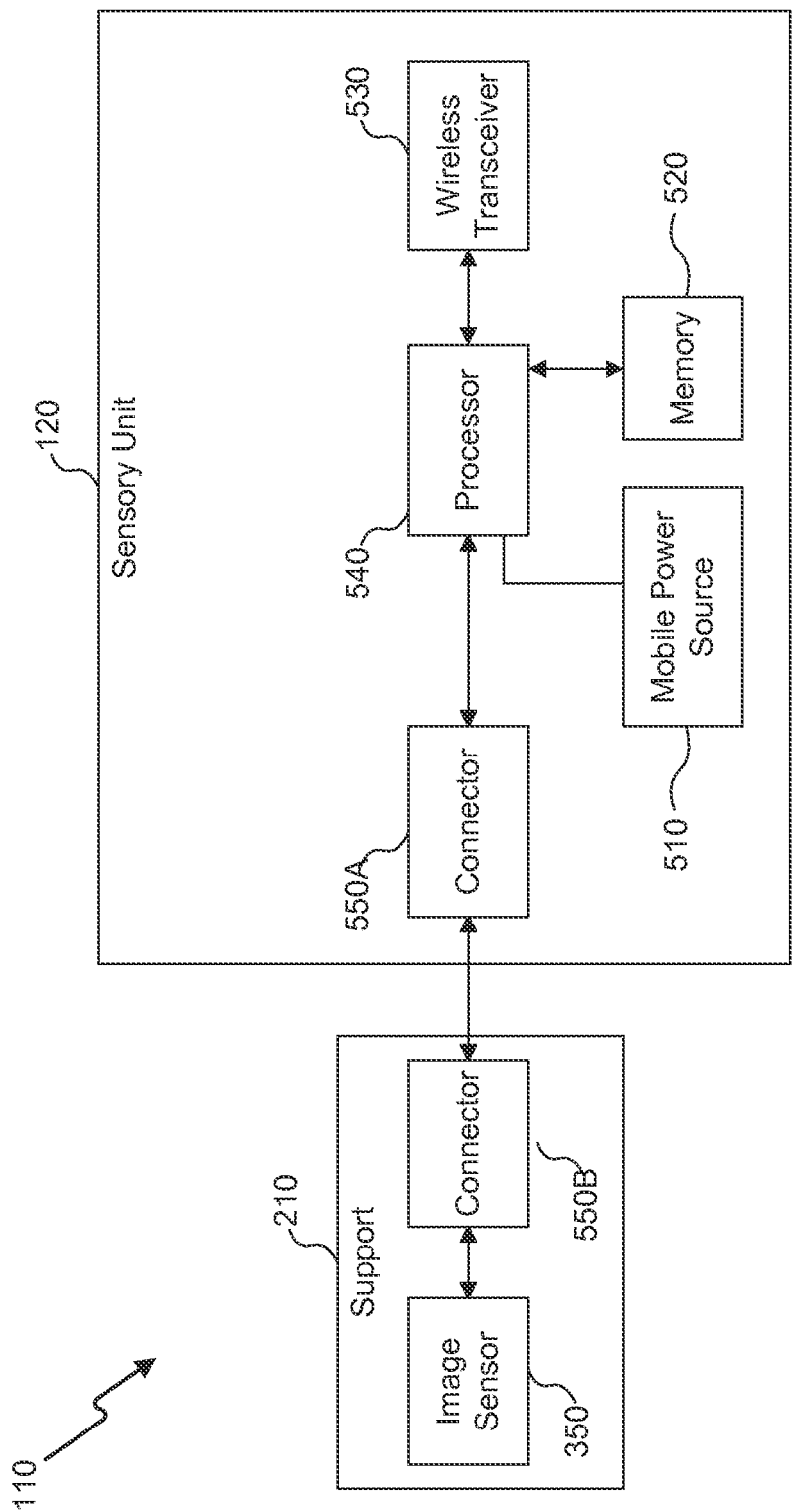
FIG. 5C is a block diagram illustrating an example of the components of an apparatus for aiding persons who have low vision according to a third embodiment.

FIG. 5C is a block diagram illustrating the components of apparatus 110 according to a third embodiment. In particular, FIG. 5C depicts an embodiment in which support 210 includes image sensor 350 and connector 550B. In this embodiment, sensory unit 120 provides functionality for processing data and, therefore, a separate processing unit is not needed in such a configuration.

As shown in FIG. 5C, sensory unit 120 includes processor 540, connector 550A, mobile power source 510, memory 520, and wireless transceiver 530. In this embodiment, apparatus 110 does not include a feedback-outputting unit. Accordingly, wireless transceiver 530 may communicate directly with a hearing aid (e.g., a Bluetooth® hearing aid). In addition, in this embodiment, image sensor 350 is included in support 210. Accordingly, when support 210 is initially mounted on glasses 105, image sensor 350 may acquire a set aiming direction. For example, a camera associated with image sensor 350 may be installed within support 210 in a predetermined angle in a position facing slightly downwards (e.g., 7-12 degrees from the horizon). Furthermore, connector 550A and connector 550B may allow data and power to be transmitted between support 210 and sensory unit 120.

Figure 5D:
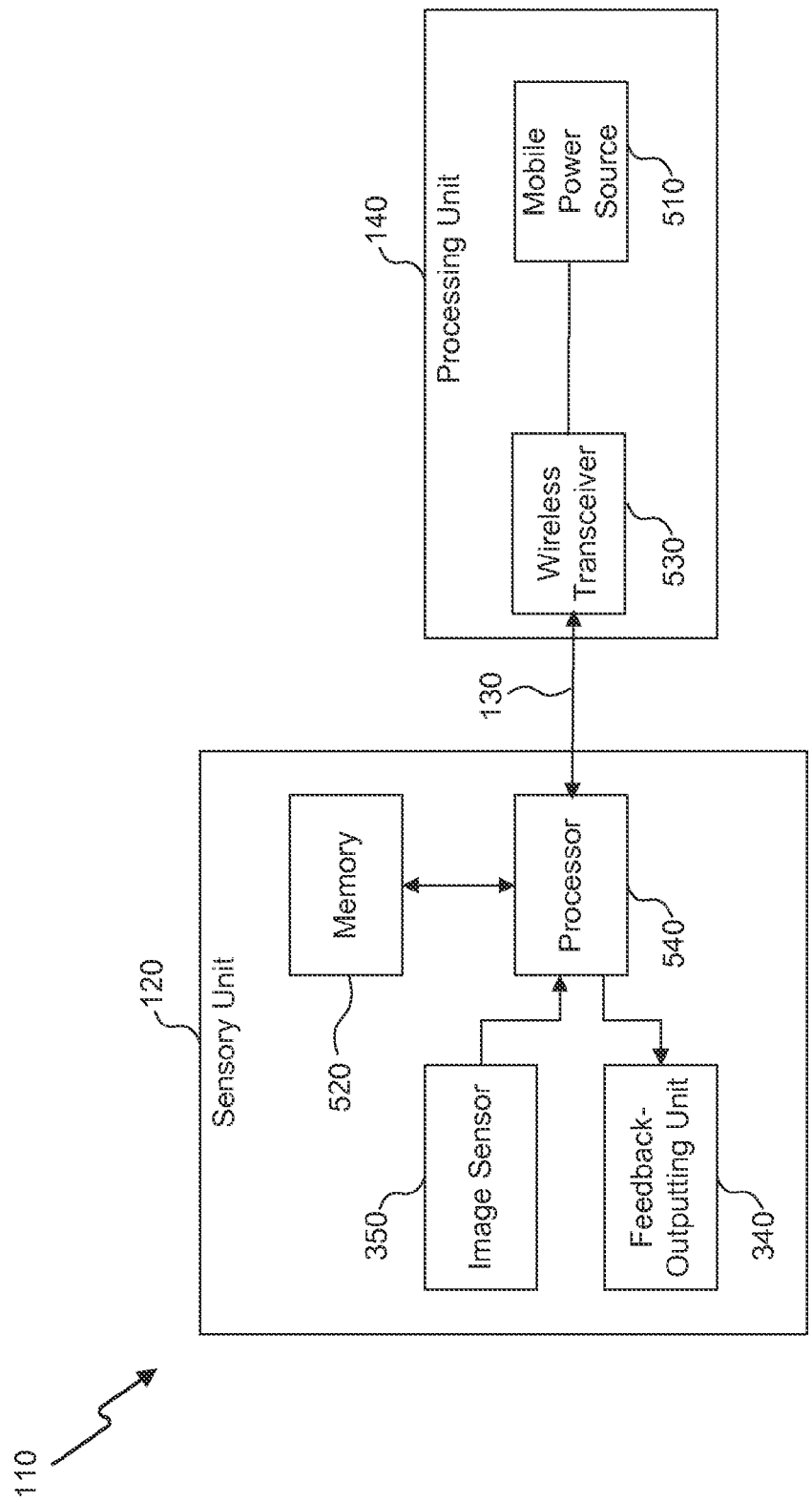
FIG. 5D is a block diagram illustrating an example of the components of an apparatus for aiding persons who have low vision according to a fourth embodiment.

FIG. 5D is a block diagram illustrating the components of apparatus 110 according to a fourth embodiment. In FIG. 5D, sensory unit 120 couples directly to a pair of glasses without the need of a support. In this embodiment, sensory unit 120 includes image sensor 350, feedback-outputting unit 340, processor 540, and memory 520. As shown in FIG. 5D, sensory unit 120 is connected via a wire 130 to processing unit 140. Additionally, in this embodiment, processing unit 140 includes mobile power source 510 and wireless transceiver 530.

As will be appreciated by a person skilled in the art having the benefit of this disclosure, numerous variations and/or modifications may be made to the disclosed embodiments. Not all components are essential for the operation of apparatus 110. Any component may be located in any appropriate part of apparatus 110 and the components may be rearranged into a variety of configurations while providing the functionality of the disclosed embodiments. Therefore, the foregoing configurations are examples and, regardless of the configurations discussed above, apparatus 110 can assist persons who have low vision with their everyday activities in numerous ways.

One way apparatus 110 can assist persons who have low vision is by identifying relevant objects in an environment. For example, in some embodiments, processor 540 may execute one or more computer algorithms and/or signal-processing techniques to find objects relevant to user 100 in image data captured by sensory unit 120. The term "object" refers to any physical object, person, text, or surroundings in an environment.

In one embodiment, apparatus 110 can perform a hierarchical object identification process. In a hierarchical object identification process, apparatus 110 can identify objects from different categories (e.g., spatial guidance, warning of risks, objects to be identified, text to be read, scene identification, and text in the wild) of image data. For example, apparatus 110 can perform a first search in the image data to identify objects from a first category, and after initiating the first search, execute a second search in the image data to identify objects from a second category.

In another embodiment, apparatus 110 can provide information associated with one or more of the objects identified in image data. For example, apparatus 110 can provide information such as the name of an individual standing in front of user 100. The information may be retrieved from a dynamic database stored in memory 520. If the database does not contain specific information associated with the object, apparatus 110 may provide user 100 with nonvisual feedback indicating that a search was made, but the requested information was not found in the database. Alternatively, apparatus 110 may use wireless transceiver 530 to search for and retrieve information associated with the object from a remote database (e.g., over a cellular network or Wi-Fi connection to the Internet).

Another way apparatus 110 can assist persons who have low vision is by performing a continuous action that relates to an object in an environment. A continuous action may involve providing continuous feedback regarding the object. For example, apparatus 110 can provide continuous feedback associated with an object identified within a field-of-view of image sensor 350, and suspend the continuous feedback when the object moves outside the field-of-view of image sensor 350. Examples of continuous feedback may include audibly reading text, playing a media file, etc. In addition, in some embodiments, apparatus 110 may provide continuous feedback to user 100 based on information derived from a discrete image or based on information derived from one or more images captured by sensory unit 120 from the environment of user 100.

Another type of continuous action includes monitoring the state of an object in an environment. For example, in one embodiment, apparatus 110 can track an object as long as the object remains substantially within the field-of-view of image sensor 350. Furthermore, before providing user 100 with feedback, apparatus 110 may determine whether the object is likely to change its state. If apparatus 110 determines that the object is unlikely to change its state, apparatus 110 may provide a first feedback to user 100. For example, if user 100 points to a road sign, apparatus 110 may provide a first feedback that comprises a descriptor of the road sign. However, if apparatus 110 determines that the object is likely to change its state, apparatus 110 may provide a second feedback to user 100 after the object has changed its state. For example, if user 100 points at a traffic light, the first feedback may comprise a descriptor of the current state of the traffic light (e.g., the traffic light is red) and the second feedback may comprise a descriptor indicating that the state of traffic light has changed (i.e., the traffic light is now green).

Apparatus 110 may also determine that an object that is expected to change its state is not functioning and provide appropriate feedback. For example, apparatus 110 may provide a descriptor indicating that a traffic light is broken.

Apparatus 110 can also assist persons who have low vision by making intelligent decisions regarding a person's intentions. Apparatus 110 can make these decisions by understanding the context of a situation. Accordingly, disclosed embodiments may retrieve contextual information from captured image data and adjust the operation of apparatus 110 based on at least the contextual information. The term "contextual information" (or "context") refers to any information having a direct or indirect relationship with an object in an environment. In some embodiments, apparatus 110 may retrieve different types of contextual information from captured image data. One type of contextual information is the time and/or the place that an image of the object was captured. Another example of a type of contextual information is the meaning of text written on the object. Other examples of types of contextual information include the identity of an object, the type of the object, the background of the object, the location of the object in the frame, the physical location of the user relative to the object, etc.

In an embodiment, the type of contextual information that is used to adjust the operation of apparatus 110 may vary based on objects identified in the image data and/or the particular user who wears apparatus 110. For example, when apparatus 110 identifies a package of cookies as an object, apparatus 110 may use the location of the package (i.e., at home or at the grocery store) to determine whether or not to read the list of ingredients aloud. Alternatively, when apparatus 110 identifies a signboard identifying arrival times for trains as an object, the location of the sign may not be relevant, but the time that the image was captured may affect the output. For example, if a train is arriving soon, apparatus 110 may read aloud the information regarding the coming train. Accordingly, apparatus 110 may provide different responses depending on contextual information.

Apparatus 110 may use contextual information to determine a processing action to execute or an image resolution of image sensor 350. For example, after identifying the existence of an object, contextual information may be used to determine if the identity of the object should be announced, if text written on the object should be audibly read, if the state of the object should be monitored, or if an image representation of the object should be saved. In some embodiments, apparatus 110 may monitor a plurality of images and obtain contextual information from specific portions of an environment. For example, motionless portions of an environment may provide background information that can be used to identify moving objects in the foreground.

Yet another way apparatus 110 can assist persons who have low vision is by automatically carrying out processing actions after identifying specific objects and/or hand gestures in the field-of-view of image sensor 350. For example, processor 540 may execute several actions after identifying one or more triggers in image data captured by apparatus 110. The term "trigger" includes any information in the image data that may cause apparatus 110 to execute an action. For example, apparatus 110 may detect as a trigger a finger of user 100 pointing to one or more coins. The detection of this gesture may cause apparatus 110 to calculate a sum of the value of the one or more coins. As another example of a trigger, an appearance of an individual wearing a specific uniform (e.g., a policeman, a fireman, a nurse) in the field-of-view of image sensor 350 may cause apparatus 110 to make an audible indication that this particular individual is nearby.

In some embodiments, the trigger identified in the image data may constitute a hand-related trigger. The term "hand-related trigger" refers to a gesture made by, for example, the user's hand, the user's finger, or any pointed object that user 100 can hold (e.g., a cane, a wand, a stick, a rod, etc.).

In other embodiments, the trigger identified in the image data may include an erratic movement of an object caused by user 100. For example, unusual movement of an object can trigger apparatus 110 to take a picture of the object. In addition, each type of trigger may be associated with a different action. For example, when user 100 points to text, apparatus 110 may audibly read the text. As another example, when user 100 erratically moves an object, apparatus 110 may audibly identify the object or store the representation of that object for later identification.

Apparatus 110 may use the same trigger to execute several actions. For example, when user 100 points to text, apparatus 110 may audibly read the text. As another example, when user 100 points to a traffic light, apparatus 110 may monitor the state of the traffic light. As yet another example, when user 100 points to a branded product, apparatus 110 may audibly identify the branded product. Furthermore, in embodiments in which the same trigger is used for executing several actions, apparatus 110 may determine which action to execute based on contextual information retrieved from the image data. In the examples above, wherein the same trigger (pointing to an object) is used, apparatus 110 may use the type of the object (text, a traffic light, a branded product) to determine which action to execute.

To assist user 100 throughout his or her daily activities, apparatus 100 may follow several procedures for saving processing resources and prolonging battery life. For example, apparatus 110 can use several image resolutions to form images. Higher image resolution provides more detailed images, but requires more processing resources. Lower image resolution provides less detailed images, but saves processing resources. Therefore, to prolong battery life, apparatus 110 may have rules for capturing and processing high resolution image under certain circumstances, and rules for capturing and processing low resolution image when possible. For example, apparatus 110 may capture higher resolution images when performing Optical Character Recognition (OCR), and capture low resolution images when searching for a trigger.

One of the common challenges persons with low vision face on a daily basis is reading. Apparatus 110 can assist persons who have low vision by audibly reading text that is present in user 100 environment. Apparatus 110 may capture an image that includes text using sensory unit 120. After capturing the image, to save resources and to process portions of the text that are relevant to user 100, apparatus 110 may initially perform a layout analysis on the text. The term "layout analysis" refers to any process of identifying regions in an image that includes text. For example, layout analysis may detect paragraphs, blocks, zones, logos, titles, captions, footnotes, etc.

In one embodiment, apparatus 110 can select which parts of the image to process, thereby saving processing resources and battery life. For example, apparatus 110 can perform a layout analysis on image data taken at a resolution of one megapixel to identify specific areas of interest within the text. Subsequently, apparatus 110 can instruct image sensor 350 to capture image data at a resolution of five megapixels to recognize the text in the identified areas. In other embodiments, the layout analysis may include initiating at least a partial OCR process on the text.

In another embodiment, apparatus 110 may detect a trigger that identifies a portion of text that is located a distance from a level break in the text. A level break in the text represents any discontinuity of the text (e.g., a beginning of a sentence, a beginning of a paragraph, a beginning of a page, etc.). Detecting this trigger may cause apparatus 110 to read the text aloud from the level break associated with the trigger. For example, user 100 can point to a specific paragraph in a newspaper and apparatus 110 may audibly read the text from the beginning of the paragraph instead of from the beginning of the page.

In addition, apparatus 110 may identify contextual information associated with text and cause the audible presentation of one portion of the text and exclude other portions of the text. For example, when pointing to a food product, apparatus 110 may audibly identify the calorie value of the food product. In other embodiments, contextual information may enable apparatus 110 to construct a specific feedback based on at least data stored in memory 520. For example, the specific feedback may assist user 100 to fill out a form (e.g., by providing user 100 audible instructions and details relevant to a form in the user's field-of-view).

To improve the audible reading capabilities of apparatus 110, processor 540 may use OCR techniques. The term "optical character recognition" includes any method executable by a processor to retrieve machine-editable text from images of text, pictures, graphics, etc. OCR techniques and other document recognition technology typically use a pattern matching process to compare the parts of an image to sample characters on a pixel-by-pixel basis. This process, however, does not work well when encountering new fonts, and when the image is not sharp. Accordingly, apparatus 110 may use an OCR technique that compares a plurality of sets of image regions that are proximate to each other. Apparatus 110 may recognize characters in the image based on statistics relate to the plurality of the sets of image regions. By using the statistics of the plurality of sets of image regions, apparatus 110 can recognize small font characters defined by more than four pixels e.g., six or more pixels. In addition, apparatus 110 may use several images from different perspectives to recognize text on a curved surface. In another embodiment, apparatus 110 can identify in image data an existence of printed information associated with a system command stored in a database and execute the system command thereafter. Examples of a system command include: "enter training mode," "enter airplane mode," "backup content," "update operating system," etc.

The disclosed OCR techniques may be implemented on various devices and systems and are not limited to use with apparatus 110. For example, the disclosed OCR techniques provide accelerated machine reading of text. In one embodiment, a system is provided for audibly presenting a first part of a text from an image, while recognizing a subsequent part of the text. Accordingly, the subsequent part may be presented immediately upon completion of the presentation of the first part, resulting in a continuous audible presentation of standard text in less than two seconds after initiating OCR.

As is evident from the foregoing, apparatus 110 may provide a wide range of functionality. More specifically, embodiments consistent with the present disclosure may provide a system, an apparatus, and a method for processing a text and for accelerating machine reading of the text.

In some embodiments, text processing and accelerated text reading may be implemented using apparatus 110 with software instructions loaded into memory 520. The software instructions, when executed by processor 540, may perform various functions related to text recognition. FIG. 6 is a block diagram illustrating an example of a set of software instructions, organized in functional modules, which can be loaded into memory 520 for processing text and accelerating machine reading of the text.

Referring to FIG. 6, memory 520 may store an OCR module 610, which may include software instructions for perform OCR processing. OCR module 610 can generate a recognized representation of a text based on an image that includes the text. The recognized representation of the text may include a collection of letters, words, phrases, sentences, or any other suitable semantic symbols. In some embodiments, the recognized representation of the text may include audible reading of the text. The image containing the text may include a static image, a frame of a video stream, or any other graphical forms that contain at least a part of the text.

Memory 520 may store an audible presentation module 620, which may include software instructions for performing an audible presentation, such as reading aloud, of the recognized representation of the text generated by the OCR module 610. Audible presentation module 620 may execute the software instructions to perform an audible presentation after at least a part of the text has been recognized by OCR module 610. In some embodiments, audible presentation module 620 may simultaneously perform an audible presentation of the first part of the text while OCR module 610 is recognizing the second part of the text.

Memory 520 may store an input/output (I/O) module 630, which may include software instructions for performing image capture, audio output, user selection, or similar functions. For example, I/O module 630 may perform image capture from image sensor 350. In another example, I/O module 630 may perform audible feedback through feedback-outputting unit 340.

Memory 520 may store a database 640. Database 640 may contain data related to OCR, audible presentation, and/or input/output functions. For example, database 640 may store data of images or frames captured by image sensor 350 to be recognized by OCR module 610. Database 640 may store recognized representation generated by OCR module 610. Database 640 may store audible data to be presented to user 100 through feedback-outputting unit 340. Other forms of data related to the functions performed by modules 610, 620, and 630, including transitional or temporary data, may also be stored in database 640.

In other embodiments, database 640 may be located remotely from memory 520, and be accessible to other components of apparatus 110 (e.g., processing unit 140) via one or more wireless connections (e.g., a wireless network). While one database is shown, it should be understood that several separate and/or interconnected databases may make up database 640. Database 640 may include computing components (e.g., database management system, database server, etc.) configured to receive and process requests for data stored in memory devices associated with database 640 and to provide data from database 640.

OCR module 610, audible presentation module 620, and input/output module 630 may be implemented in software, hardware, firmware, a mix of any of those, or the like. For example, if OCR module 610, audible presentation module 620, and input/output module 630 are implemented in software, they may be stored in memory 520, as shown in FIG. 6. Other components of processing unit 140 and/or sensory unit 120 may be configured to perform processes to implement and facilitate operations of OCR module 610, audible presentation module 620, and input/output module 630. Thus, OCR module 610, audible presentation module 620, and input/output module 630 may include software, hardware, or firmware instructions (or a combination thereof) executable by one or more processors (e.g., processor 540), alone or in various combinations with each other. For example, OCR module 610, audible presentation module 620, and input/output module 630 may be configured to interact with each other and/or other modules of apparatus 110 to perform functions consistent with disclosed embodiments. In some embodiments, any of the disclosed modules (e.g., OCR module 610, audible presentation module 620, and input/output module 630) may each include dedicated sensors (e.g., IR, image sensors, etc.) and/or dedicated application processing devices to perform the functionality associated with each module.

In some embodiments, a system for perform accelerated machine reading of text may include an apparatus, e.g., apparatus 110. As described above, apparatus 110 may include processor 540 and memory 520. When user 100 uses apparatus 110 to recognize text, an image containing the text may be captured by apparatus 110. For example, image sensor 350 may be used to capture the image. The image may be a graphical presentation of one or more objects in an environment of user 100. For example, the image may be an image of a newspaper, a book, a flyer, a poster, a sign, a note, etc., or at least a part thereof or a combination thereof. The image may contain a plurality of elements, such as figure, text, etc.

Figure 7A:
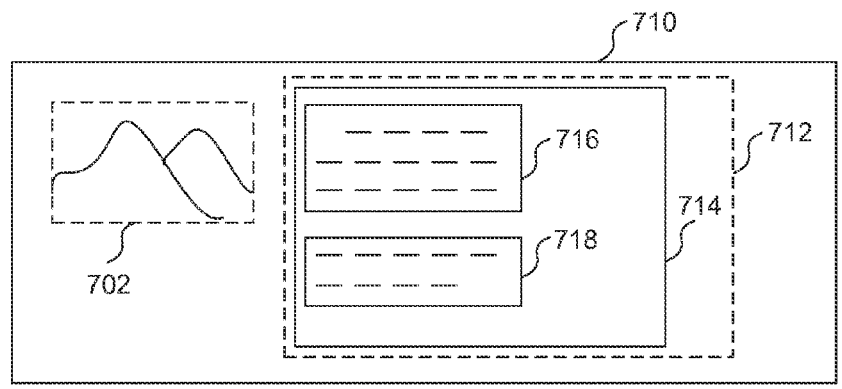
FIGS. 7A-7C are schematic illustrations of exemplary images containing text.
Figure 7B:
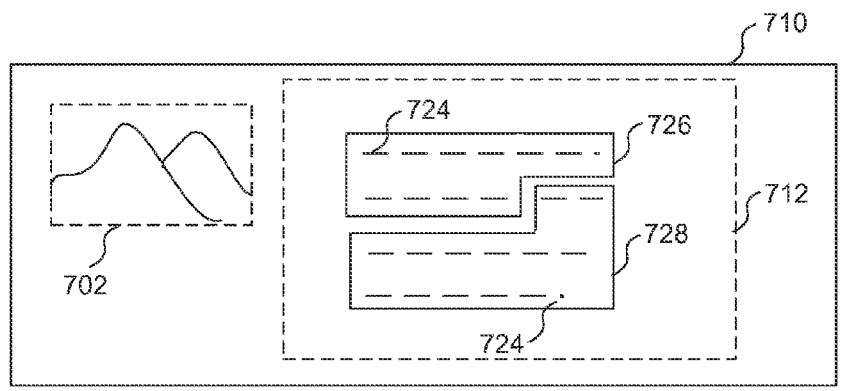
Figure 7C:
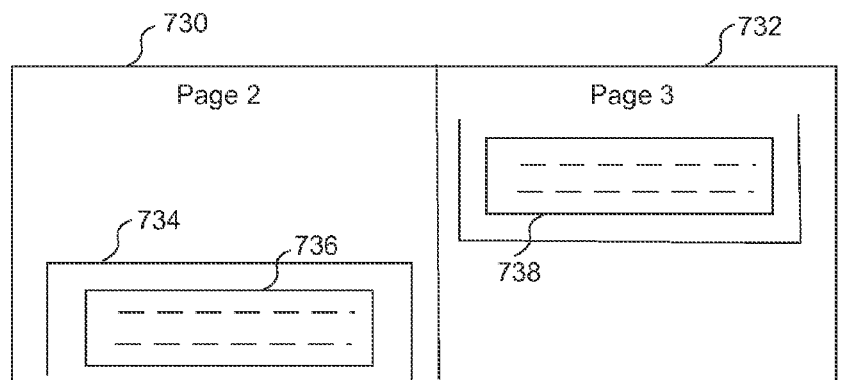

FIGS. 7A-7C are schematic illustrations of some exemplary images containing text. In FIG. 7A, image 710 may be an image of a newspaper, a book, a magazine, a poster, etc. Image 710 may contain a plurality of elements. For example, image 710 may contain a figure section 702. Figure section 702 may contain one or more graphical figures, such as a photo, a cartoon, an illustration, etc. Image 710 may contain a text section 712. Text section 712 may contain text, symbol, or other semantic representations. It is noted that figure section 702 and text section 712 may be intertwined with each other, such as in an advertisement or in a magazine cover. Therefore, figure section 702 and text section 712 are denoted in dashed lines to indicate that they are not necessarily separate sections. Text section 712 may include a text passage 714. Text passage 714 may include a paragraph of text, a section of text, one or more rows/columns of text, or any other forms of collection of text characters that can be grouped together. In one example, text passage 714 may be a logical collection of text characters, such as a paragraph of text that may run on one or more pages. In another example, text passage 714 may be a physical collection of text characters, such as text within a text box, within a callout region, within a marginal area, etc., which may or may not form a paragraph.

Text passage 714 may include multiple portions of text, such as text portions 716 and 718. A portion of text may be any subset of text passage 714. For example, text portions 716 and 718 may be substantially equal in terms of the number of characters. In another example, text portion 716 may contain more or less characters than text portion 718. For instance, text portion 716 may contain the first sentence or the first line of text passage 714, and text portion 718 may contain the subsequent sentence or the subsequent line of text passage 714. In some embodiments, text portions 716 and 718 may cover substantially all text content in text passage 714. In other embodiments, text portions 716 and 718 may cover a part of the text content in text passage 714. Text portion 718 may or may not be consecutive to text portion 716.

FIG. 7B shows an example in which text portions 726 and 728 may be parts of a same sentence 724. In some embodiments, sentence 724 may be a collection of text followed by a period, a question mark, or other punctuation marks that end a sentence. In other embodiments, sentence 724 may be a collection of text without any punctuation mark. In some embodiments, text portions 726 and 728 may cover substantially all text content of sentence 724. In other embodiments, text portions 726 and 728 may cover a part of the text content of sentence 724. Text portion 728 may or may not be consecutive to text portion 726.

FIG. 7C shows another example in which text portions 736 and 738 may be on different pages. In FIG. 7C, a text passage 734 may run across two pages 730 and 732. Text portion 736 may be on page 730 and text portion 738 may be on page 732. In some embodiments, text portion 736/738 may cover substantially all text content of text passage 734 that is on page 730/732, respectively. In other embodiments, text portion 736/738 may cover a part of text content of text passage 734 that is on page 730/732, respectively. Text portion 738 may or may not be consecutive to text portion 736.

When processor 540 performs OCR and audible presentation of text in an image, such as text passage 714 in image 710, processor 540 may break up text passage 714 into multiple portions, such as text portions 716 and 718, to accelerate the audible presentation process and to avoid delay between the moment when user 100 triggers a text recognition process and the moment when apparatus 110 starts to audibly read the text. For example, instead of performing OCR on the entire text content of passage 714 and starting to audibly read after all text characters have been recognized, apparatus 110 may be configured to perform OCR on text portion 716 first and start to audibly read text portion 716 right after text in portion 716 has been recognized, and while audibly reading text portion 716, simultaneously perform OCR on text portion 718. If the length of text portion 716 is properly controlled, audible reading can be started in a relatively short time period after user 100 triggers text recognition. In the following paragraphs, several embodiments will be described to implement the accelerated text reading technique.

Figure 8A:
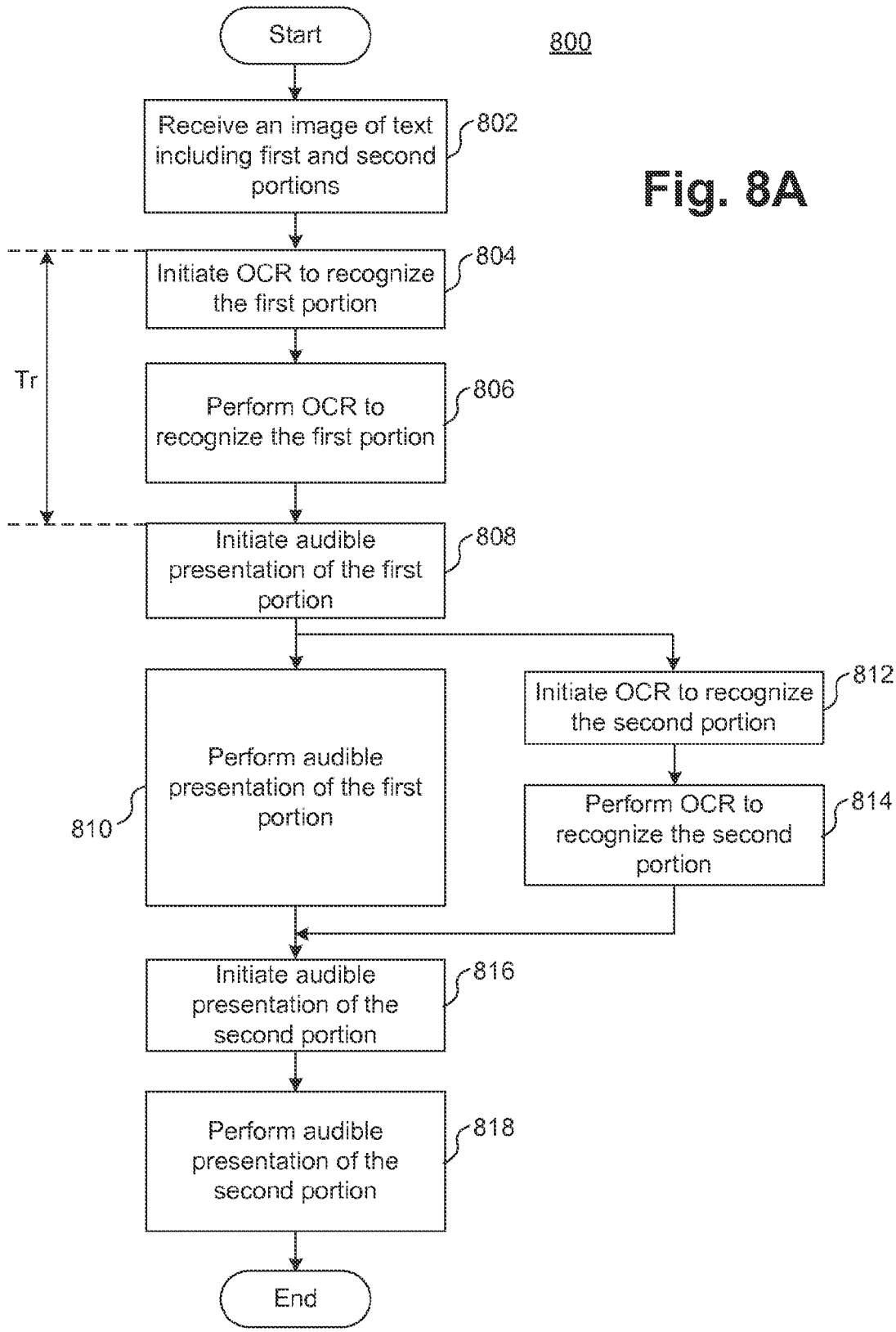
FIG. 8A is a flow chart of an exemplary process for accelerating machine reading of text, according to a first embodiment.

FIG. 8A is a flow chart of an exemplary process 800 for accelerating machine reading of text, according to a first embodiment. In step 802, processor 540 may be configured to receive an image of text (e.g., image 710) to be audibly read. Image 710 may include a first portion (e.g., portion 716) and a second portion (e.g., portion 718). For example, processor 540 may execute software instructions stored in I/O module 630 to receive image 710 captured by image sensor 350. In some embodiments, processor 540 may receive image 710 after user 100 triggers text recognition by, for example, pointing to a text, make an audible command, etc.

In step 804, processor 540 may initiate an OCR process to recognize text contained in text portion 716. As used herein, by initiating a process, it is meant that processor 540 starts the process. The action of initiation is complete after the process starts, but does not necessarily require the process to finish. For example, step 804 is considered complete after the OCR process starts. Step 804 is followed by step 806, in which processor 540 performs the OCR process to recognize text in text portion 716. Both steps 804 and 805 may be performed by processor 540 by executing software instructions stored in OCR module 610.

After processor 540 finishes the OCR process on text portion 716, process 800 proceeds to step 808, in which processor 540 initiates audible presentation of the recognized text of text portion 716. Processor 540 may execute software instructions stored in audible presentation module 620 to initiate the audible reading of the recognized text to user 100. For example, processor 540 may generate audible reading signals (e.g., analog and/or digital signals) based on the recognized text of text portion 716 using a text-to-voice algorithm stored in audible presentation module 620. The audible reading signals may then be transmitted to feedback outputting unit 340 through wire 130 or via a wireless communication channel established between wireless transceiver pair 530A and 530B. Feedback outputting unit 340 may convert the audible reading signals to audible feedback (e.g., readout, notification sound, vibration, etc.) to user 100 (e.g., using a speaker or a bone conduction headphone). In some embodiments, step 808 is immediately performed after OCR process on text portion 716 finishes. A time parameter Tr, referred to as the response time, may be used to measure the time interval from initiating OCR process on text portion 716 to initiating audible presentation of text portion 716. Response time Tr may be a measure of delay time experienced by user 100 after he triggers text recognition. In some embodiments, Tr may be controlled to be less than four seconds, less than two seconds, less than one second, or even shorter. An exemplary method of shortening Tr is to limit the number of characters in text portion 716. For example, text portion 716 may contain the first sentence, the first line, or even the first several words of text passage 714. As a result, the corresponding OCR process may take a relatively short period of time to finish.

After processor 540 initiates the audible presentation of text portion 716 (e.g., step 808 is complete), process 800 proceeds into two parallel branches. In one branch, as indicated by step 810, processor 540 performs the action to audibly present text portion 716 after the action is initiated in step 808. Similar to step 808, processor 540 may execute software instructions stored in audible presentation module 620 to audibly read the recognized text to user 100. In the other branch, as indicated by steps 812 and 814, processor 540 simultaneously initiates and performs OCR on the second portion of text, e.g., text portion 718. Depending on the length of text portion 716, the speed of audible reading, and the length of text portion 718, the OCR process on text portion 718 may finish before the completion of the audible presentation of text portion 716. In this case, process 800 may proceed to step 816, in which the audible presentation of text portion 718 is initiated automatically and immediately upon the completion of step 810. Then in step 818, processor 540 may perform the audible presentation of text portion 718 to user 100. User 100 can experience a seamless transition between the reading of text portion 716 and text portion 718 and enjoy a continuous reading of text without further delay.

It is noted that to provide continuous reading of text, method 800 may include additional steps similar to steps 810, 812, and 814 that are performed simultaneously in a staggered manner. For example, after step 814 finishes, processor 540 may receive a portion of text (e.g., a third portion) next to or subsequent to text portion 718 and initiate/perform OCR on the third portion at the same time when step 810, 816, and/or 818 is performed. Then, after step 818 finishes, processor 540 may initiate/perform audible reading of the third portion if the OCR process on the third portion is completed. The length of the text portion can be dynamically controlled such that whenever the reading of a text portion is finished, the next portion of text would be ready to read. In this way, user 100 is able to enjoy a continuous reading of text. In some embodiments, user 100 may not be even required to provide additional triggers after the first trigger.

In some embodiments, in order to improve user experience, the delay between the triggering of text recognition and starting of audible reading can be controlled to be within a tolerance threshold. In particular, response time Tr can be used as a condition parameter to start the audible presentation process.

FIG. 8B is a flow chart of such an exemplary process 820 for accelerating machine reading of text, according to a second embodiment. In FIG. 8B, steps 822 and 824 are similar to steps 802 and 804 of FIG. 8A. In step 826, while processor 540 is performing OCR on the first portion (e.g., text portion 716), a condition is checked (step 828) to determine if response time Tr is longer than a threshold time Ts. The condition can be checked periodically during the course of performing OCR process on the first portion. Threshold time Ts may have a predetermined value, such as four seconds, two seconds, one second, etc. If Tr is not longer than Ts, then process 820 proceed back to step 826 to continue performing OCR until the next check of condition 828. If Tr is longer than Ts, the process 820 proceed to step 830, in which an audible presentation of the recognized part of the first text portion is initiated. Then in step 832, processor 540 performs the audible presentation of the recognized part. It is noted that the OCR step (e.g., step 826) and the audible presentation steps (e.g., steps 830 and 832) may be performed simultaneously. The recognized text, such as characters, words, phrases, etc., may be continuously saved in memory 520 (e.g., database 640) as they are generated from the OCR process. In the audible presentation steps (e.g., steps 830 and 832), the recognized text may be continuously read from memory 520 and audibly presented to user 100.

After the OCR process on the first text portion is completed (e.g., step 826 finishes), process 820 proceeds to step 834, in which processor 540 initiates OCR process to recognize the second portion of text (e.g., text portion 718). Then in step 836, processor 540 performs the OCR process on the second portion. It is noted that steps 834 and 836 may be performed in parallel to step 832. During the course of performing OCR on the second portion, a condition is checked (e.g., periodically) in step 838 to determine if the audible presentation of the first portion is completed. In other words, step 838 checks if step 832 is completed. If step 832 is not completed (i.e., the "No" branch of step 838), then process 820 proceeds back to step 836 to continue performing OCR on the second portion until the next check. If step 832 is completed (i.e., the "Yes" branch of step 838), then process 820 proceeds to step 840, in which processor 540 initiates the audible presentation of the second portion. Then in step 842, processor 540 performs the audible presentation of the second portion.

Similar to process 800, the OCR process (e.g., step 826 or 836) and the audible presentation process (e.g., step 832 or 842) may be performed in a staggered manner. For simplicity a detailed description of the staggered operation in process 820 is omitted.

Figure 8C:
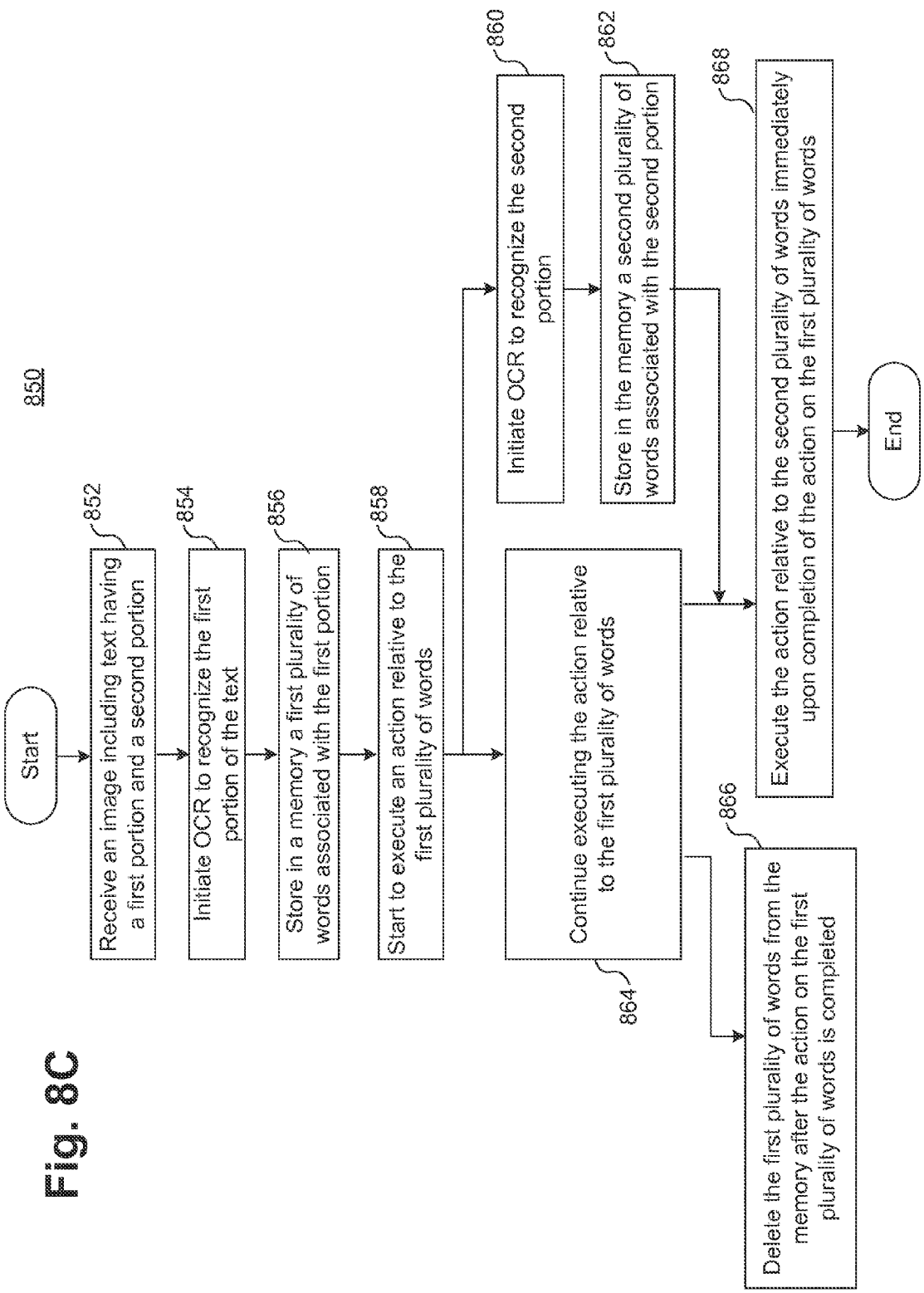
FIG. 8C is a flow chart of an exemplary process for accelerating machine reading of text, according to a third embodiment.

FIG. 8C is a flow chart of an exemplary process 850 for accelerating machine reading of text, according to a third embodiment. In FIG. 8C, steps 852 and 854 are similar to steps 802 and 804 of FIG. 8A. In step 856, as the OCR process initiated in step 854 starts to generate recognized results that associated with the first portion of text (e.g., text portion 716), such as a plurality of characters, words, phrases, etc., processor 540 stores the recognized results in memory 520 (e.g., in database 640). It is noted that the OCR process and the OCR result storage process (e.g., step 856) may be performed simultaneously. For example, step 856 may be performed after a certain number of words have been recognized. As these words being stored in memory 520, processor 540 may continue the OCR process.

After the first text portion have been recognized and the words associated with the first portion have been stored, process 850 may proceed to step 858, in which processor 540 may start to execute an action (e.g., audible presentation) relative to the stored words. For example, processor 540 may start read the stored words aloud to user 100. After step 858, processor 540 may simultaneously perform audible presentation of the recognized words associated with the first portion (e.g., step 864) and recognition of a second portion of text (e.g., text portion 718) in steps 860 and 862. For example, in step 860 processor 540 may initiate OCR process to recognize text portion 718. In step 862 processor 540 may store the recognized words associated with text portion 718 in memory 520.

After step 864 is completed, process 850 may proceed into two parallel branches. In step 868, processor 540 may perform audible presentation of the recognized words associated with text portion 718. In some embodiments, step 868 is performed immediately after the completion of step 864. In step 866, processor 540 may delete the recognized words associated with text portion 716 from memory 520 after these words have been audibly presented to user 100. Step 866 and step 868 may be performed in parallel.

Figure 8D:
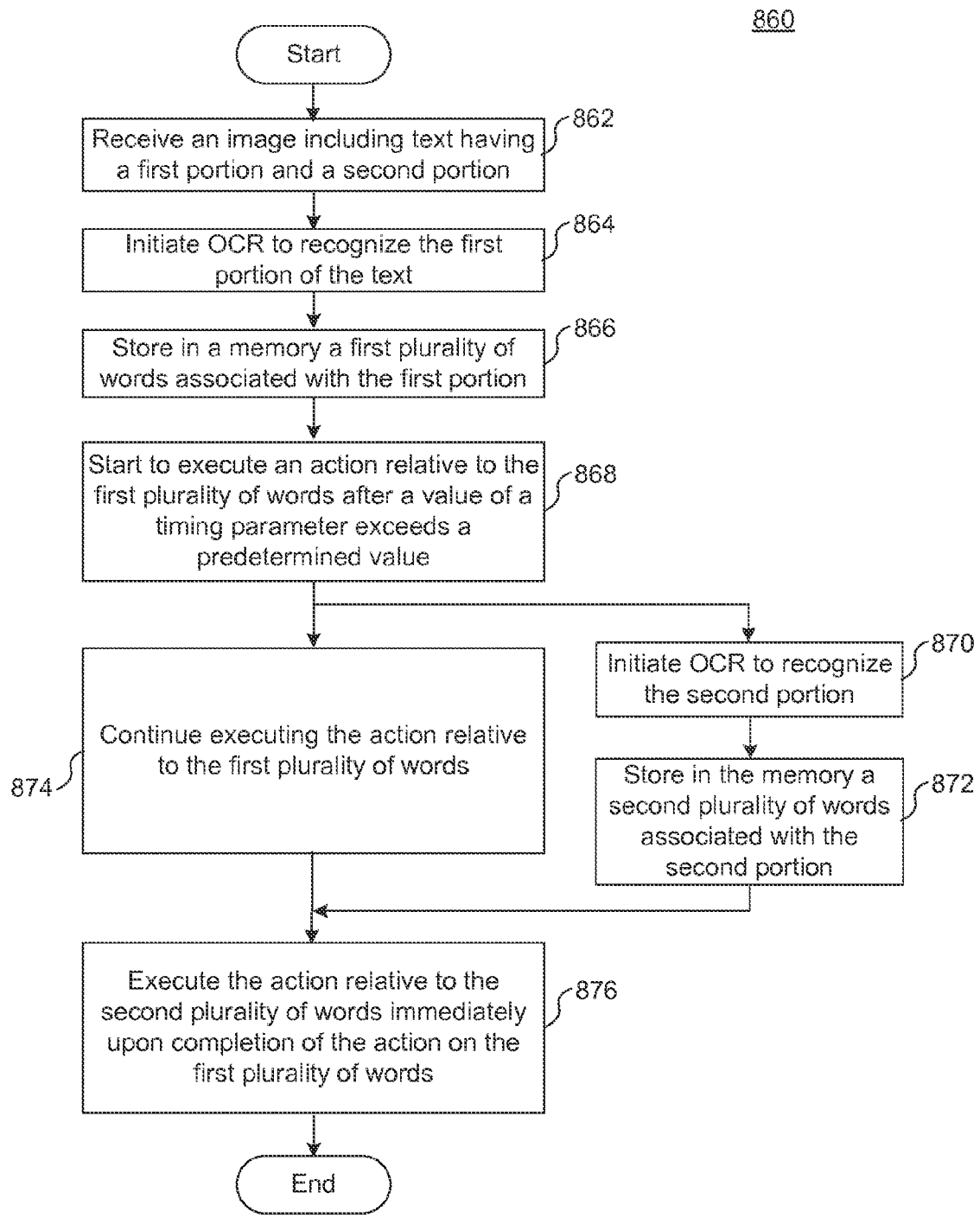
FIG. 8D is a flow chart of an exemplary process for accelerating machine reading of text, according to a fourth embodiment.

FIG. 8D is a flow chart of an exemplary process 860 for accelerating machine reading of text, according to a fourth embodiment. In FIG. 8D, steps 862, 864, and 866 are similar to steps 852, 854, and 856 of FIG. 8C. In step 868, processor 540 may periodically check a value of a timing parameter (e.g., Tr), and start to execute an action (e.g., audible presentation) relative to the recognized and stored words after Tr exceeds a predetermined value (e.g., Ts). Step 868 may be implemented in a similar manner to steps 826, 828, and 830 of FIG. 8B. After the audible presentation process is started, process 860 proceeds to steps 870, 872, 874, and 876, which are similar to steps 860, 862, 864, and 868 of FIG. 8C, respectively.

Figure 9A:
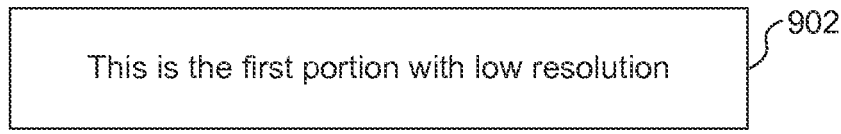
FIGS. 9A-9C are schematic illustrations of exemplary images of text portions.
Figure 9B:
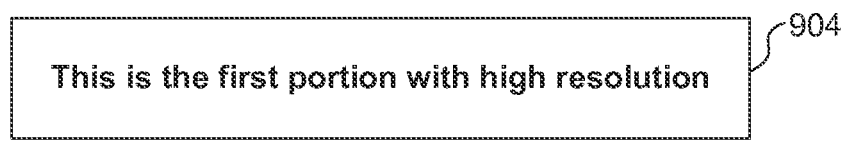
Figure 9C:
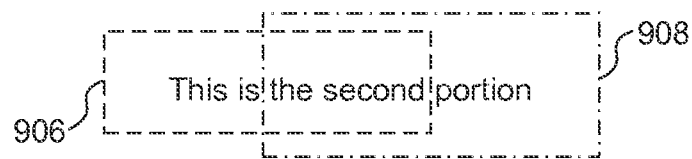

In some embodiments, multiple images may be captured and processed with respect to one text portion. FIGS. 9A-9C are illustrates some examples of such multiple images. FIG. 9A shows an image 902 of the first portion of text (e.g., text portion 716) with low resolution. FIG. 9B shows another image 904 of text portion 716 with high resolution. Images 902 and 904 may be captured by image sensor 350 using different resolution settings.

FIG. 9C shows multiple images of the second portion of text (e.g., text portion 718). Image 906 covers the left part of text portion 718, while image 908 covers the right part of text portion 718. However, none of images 906 and 908 includes all of text portion 718. The situation shown in FIG. 9C may occur when text portion 718 is on a curved surface or when text portion 718 appears on changing screens of an electronic device (e.g., computer, TV, mobile phone, etc.)

FIGS. 10A-10D are flow charts of exemplary processes for performing OCR on multiple images of a text portion. In the first exemplary process 1000 shown in FIG. 10A, in step 1002, processor 540 may initiate OCR to recognize the first image (e.g., image 902) of a text portion (e.g., text portion 716). In step 1004, processor 540 may perform OCR on image 902 to recognize text. In step 1006, processor 540 may initiate OCR to recognize the second image (e.g., image 904) of text portion 716. In step 1008, processor 540 may perform OCR on image 904 to recognize text.

After processor 540 performs OCR on images 902 and 904, processor 540 may combine the OCR results from images 902 and 904. For example, in step 1010, processor 540 may combine OCR results of low resolution image 902 and high resolution image 904 to generate a final result to audibly present to user 100.

Figure 10A:
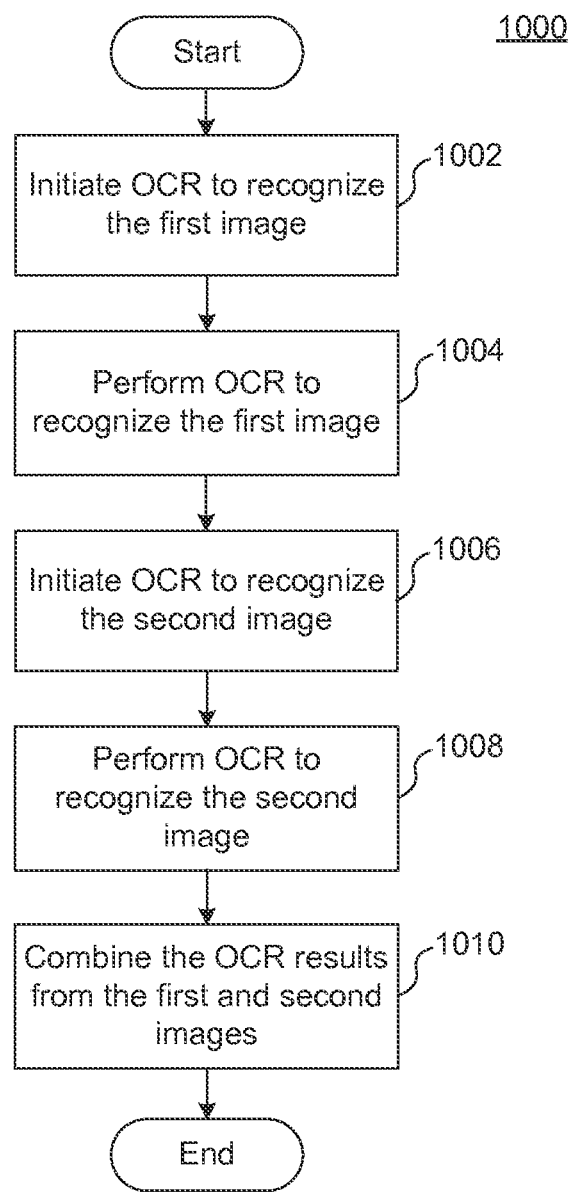
FIG. 10A is a flow chart of a first exemplary process for performing optical character recognition on multiple text images.
Figure 10B:
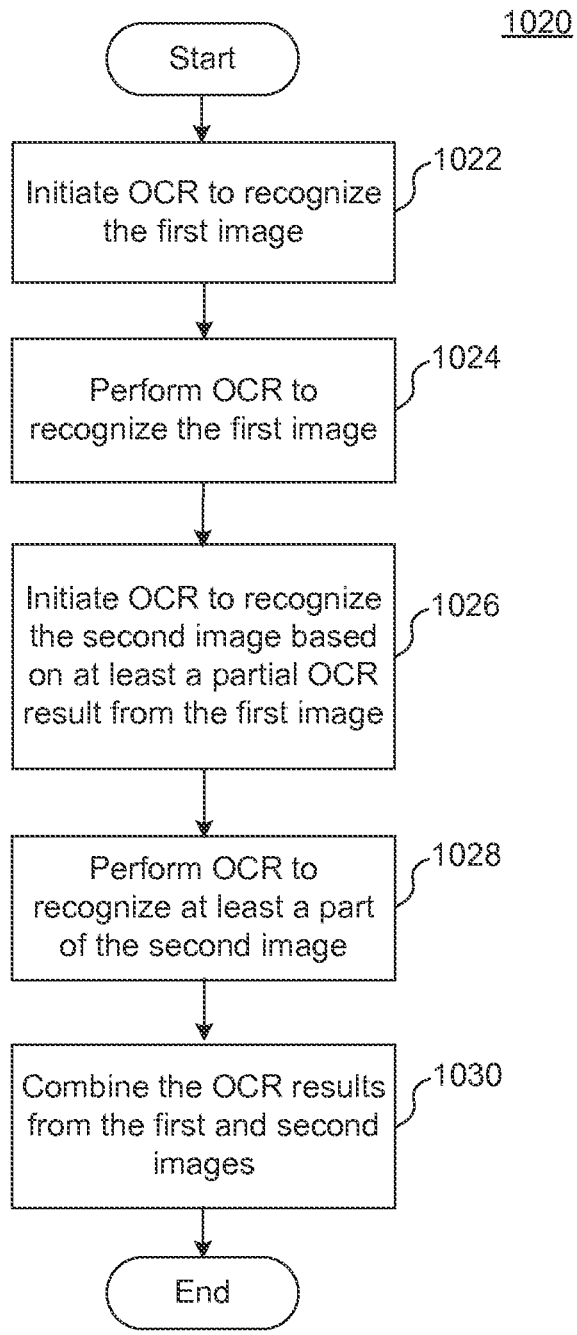
FIG. 10B is a flow chart of a second exemplary process for performing optical character recognition on multiple text images.

FIG. 10B is a flow chart of a second exemplary process 1020 for performing OCR on multiple text images. Steps 1022 and 1024 are similar to steps 1002 and 1004 of FIG. 10A. In step 1026, processor 540 may initiate OCR to recognize image 904 based on at least a partial OCR result from image 902. For example, the OCR result from image 902 may not be satisfactory due to low resolution, and only a part of text portion 716 is recognized in step 1024. Based on the partially recognized result from image 902, processor 540 may initiate OCR on image 904, which has a higher resolution than image 902, to recognize a part of (e.g., the unrecognized part of text portion 716 after step 1024) or the entire content of text portion 716. In step 1028, processor 540 may perform OCR on image 904 to recognize at least a part of image 904 (e.g., the unrecognized part of text portion 716). In step 1030, processor 540 may combine the OCR results from images 902 and 904. For example, processor 540 may combine the recognized part of image 902 with recognized part of image 904 to generate a final result to audibly present to user 100.

Figure 10C:
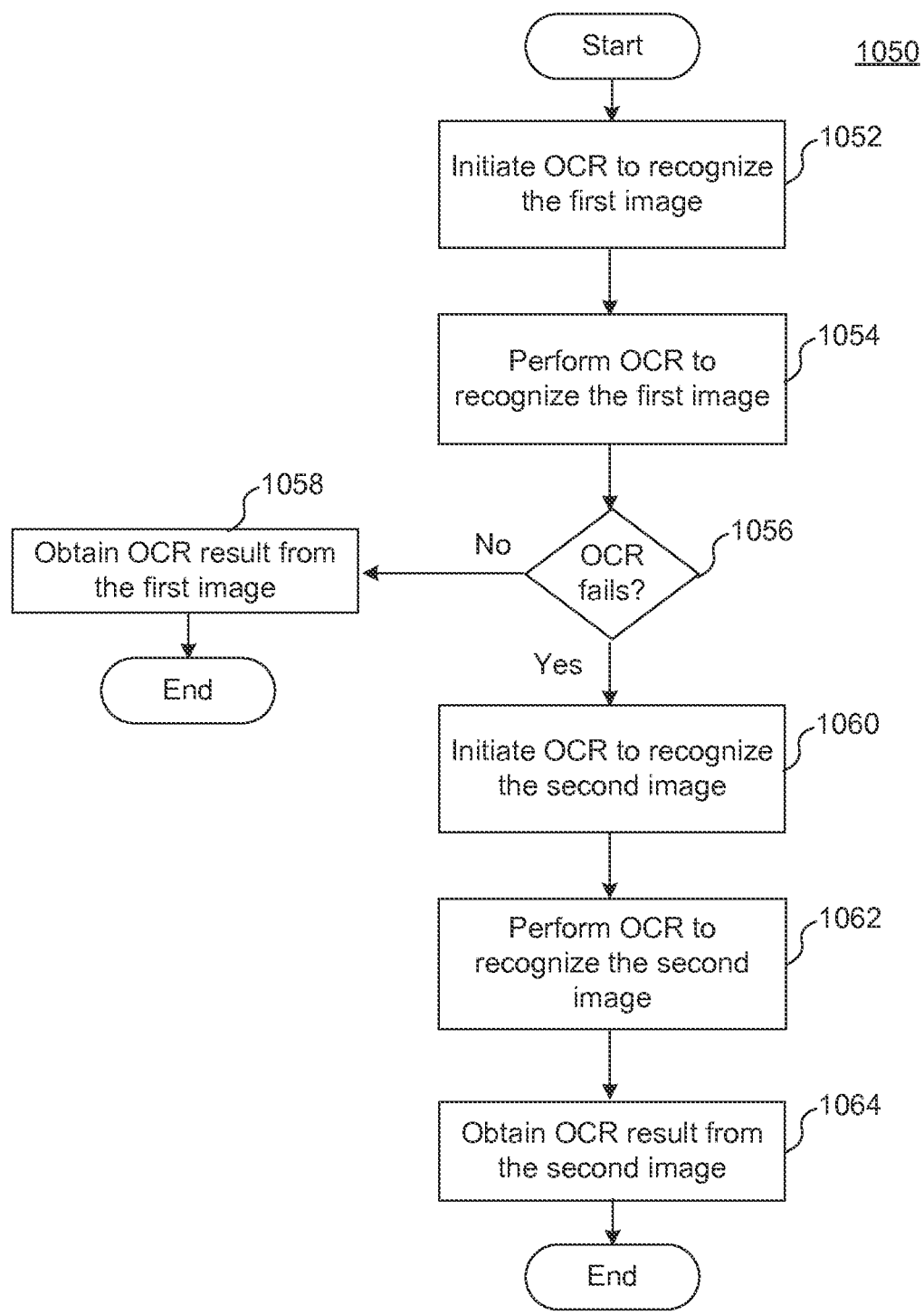
FIG. 10C is a flow chart of a third exemplary process for performing optical character recognition on multiple text images.

FIG. 10C is a flow chart of a third exemplary process 1050 for performing optical character recognition on multiple text images. Steps 1052 and 1054 are similar to steps 1002 and 1004 of FIG. 10A. In step 1056, processor 540 may determine if the OCR process performed on image 902 fails. The OCR process may be considered failed if a certain percentage (e.g., 80%, 60%, 50%, etc.) of text are not recognized. If the OCR does not fail, process 1050 proceeds to step 1058, in which processor 540 obtains an OCR result from image 902. If the OCR fails, process 1050 proceeds to step 1060. In step 1060, processor 540 initiates OCR to recognize image 904, which has a higher resolution than image 902. In step 1062, processor 540 performs OCR to recognize text in image 904. In step 1064, processor 540 obtains an OCR result from image 904.

Figure 10D:
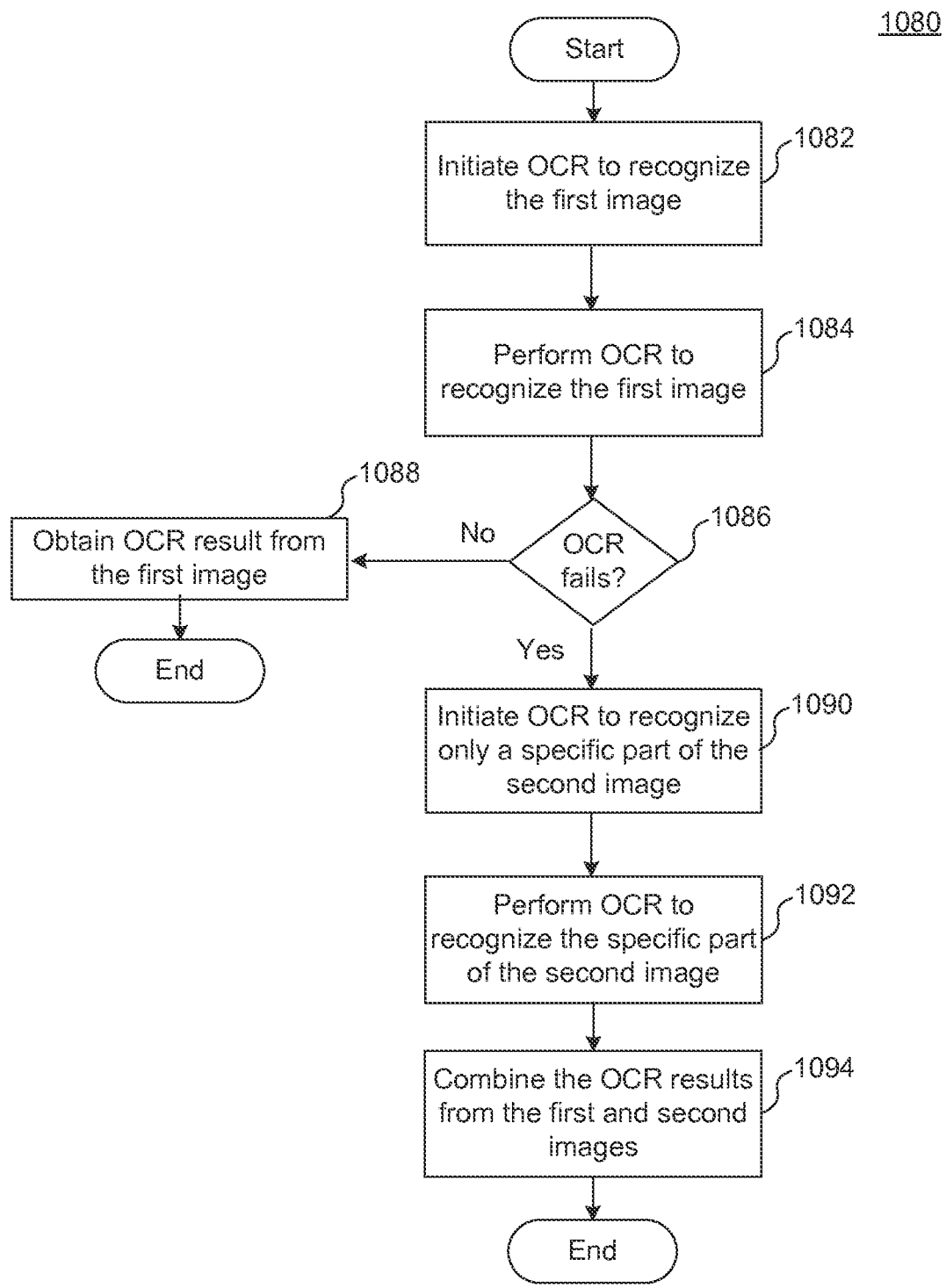
FIG. 10D is a flow chart of a fourth exemplary process for performing optical character recognition on multiple text images.

FIG. 10D is a flow chart of a fourth exemplary process for performing optical character recognition on multiple text images. Steps 1082, 1084, 1086, and 1088 are similar to steps 1052, 1054, 1056, and 1058 of FIG. 10C. In step 1090, processor 540 initiates OCR to recognize only a specific part of image 904. For example, although the OCR on image 902 is considered failed, there may be one or more parts in the OCR result from image 902 that are recognizable. Therefore, instead of performing OCR on the entire image of image 904, only one or more specific parts of image 904 are used in the OCR process in step 1090 to, for example, cover the unrecognized part(s) from the result of step 1084. In step 1092, processor 540 may perform OCR to recognize the specific part of image 904. In step 1094, processor 540 may combine the results from images 902 and 904 to generate a final result.

Figure 11:
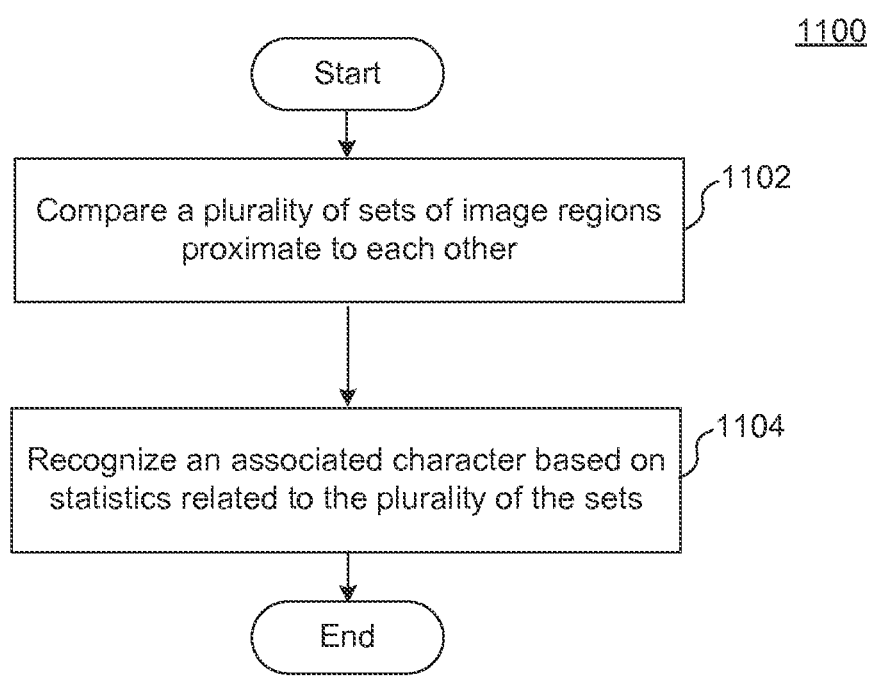
FIG. 11 is a flow chart of an exemplary process for performing optical character recognition.

FIG. 11 shows an exemplary process 1100 for performing OCR. Process 1100 may be a sub process of step 806 or 814 of FIG. 8A; step 826 or 836 of FIG. 8B; step 1004 or 1008 of FIG. 10A; step 1024 or 1028 of FIG. 10B; step 1054 or 1062 of FIG. 10C; or step 1084 or 1092 of FIG. 10D. In step 1102, processor 540 may compare a plurality of sets of image regions that are proximate to each other. For example, processor 540 may compare text regions of image to be recognized with a set of candidate image regions that have already been associated with text characters or representations. The comparison may yield likelihoods that the to-be-recognized image regions match one or more candidate image regions that have already established text association. In step 1104, processor 540 may recognize an associated character based on statistics related to the plurality of sets of image regions. For example, processor 540 may recognize a text character based on statistical results, e.g., the likelihoods of matching between the to-be-recognized image regions and the candidate image regions.

In some embodiments, processor 540 may be configured to recognize characters defined by a certain number of pixels. As used herein, a character is defined by X pixels when a substantial part of the character occupies X pixels of a digital image. It is noted that different character may occupy different number of pixels. In a black and white image, each pixel may only have a binary value (e.g., "0" or "1"; "True" or "False"; "Black" or "White"; etc.). In a gray scale image, each pixel may have a range of values indicating the degree of gray. In a color image, each pixel may have a vector value, such as (X, Y, Z), indicating the intensities of primary colors (e.g., red, green, and blue). In any case, a character in a digital image may occupy a number of pixels and the character is said to be defined by X number of pixels when a substantial part of the character occupies or covers X number of pixels. Processor 540 may be configured to perform OCR (e.g., using process 1100) to recognize characters defined by 15 or less pixels; 10 or less pixels; or even 6 or less pixels.

Figure 12A:
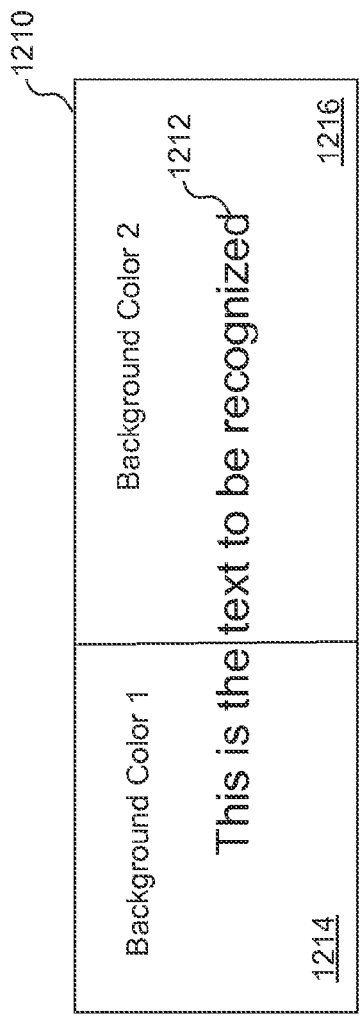
FIGS. 12A and 12B are schematic illustrations of text images having different colors.
Figure 12B:
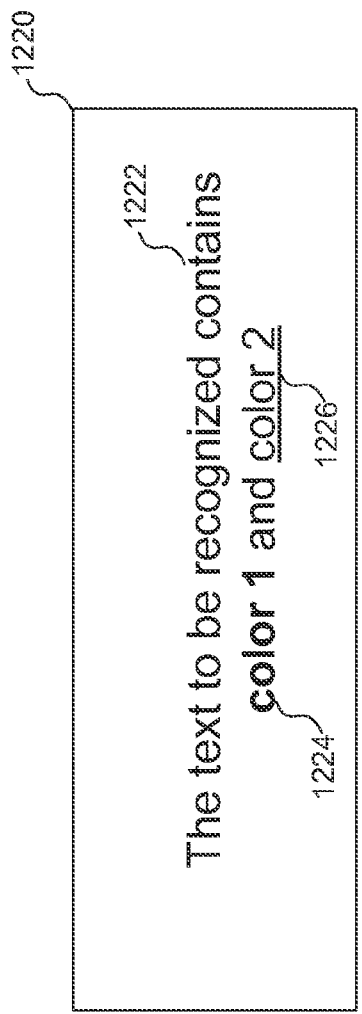

In some embodiments, processor 540 may be configured to recognize text images having different colors. FIGS. 12A and 12B are schematic illustrations of text images having different colors. In FIG. 12A, image 1210 contains text 1212. Image 1210 contains two background colors 1214 and 1216. In FIG. 12B, image 1220 contains text 1222. A part of text 1222 may have a first color 1224 and another part of text 1222 may have another color 1226. Processor 540 may be configured to recognize text 1212 or 1222 in image 1210 or 1220, respectively. In some embodiments, background or text colors may be used to indicate different text portions. For example, in FIG. 12A, text having background color 1214 (i.e., "This is the") may form a first portion (e.g., text portion 716, 726, or 736), and text having background color 1216 (i.e., "text to be recognized") may form a second portion (e.g., text portion 718, 728, or 738). In another example, referring to FIG. 12B, text having color 1224 (i.e., "color 1") may form a first portion (e.g., text portion 716, 726, or 736), and text having color 1226 (i.e., "color 2") may form a second portion (e.g., text portion 718, 728, or 738). Background or text colors may be an original color of an object (e.g., book, magazine, newspaper, etc.), or may be added/modified by user 100 (e.g., user 100 may highlight certain text). In some embodiments, processor 540 may identify different colors and use the color information to aid the OCR process.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks, floppy disks, or CD ROM, or other forms of RAM or ROM, USB media, DVD, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets. One or more of such software sections or modules can be integrated into a computer system or existing e-mail or browser software.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed routines may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A system for accelerating machine reading of text, the system comprising:
    at least one processor device configured to:
        receive at least one image of text to be audibly read;
        initiate optical character recognition to recognize the text;
        during the optical character recognition of the text, determine that an operational time of the optical character recognition exceeds a predetermined threshold;
        after determining that the operational time of the optical character recognition exceeds the predetermined threshold, initiate an audible presentation of a first portion of the text that has been recognized;
        during the audible presentation of at least part of the first portion, simultaneously perform optical character recognition to recognize a second portion of the text; and
        automatically causing the second portion of the text to be audibly presented immediately upon completion of the audible presentation of the first portion.

2. The system of claim 1, wherein the first portion and the second portion of the text are part of a same paragraph.

3. The system of claim 1, wherein the first portion and the second portion of the text are part of a same sentence.

4. The system of claim 1, wherein the first portion and the second portion of the text are included on different pages of a same passage.

5. The system of claim 1, wherein the at least one processor device is further configured to recognize characters defined by 15 or less pixels.

6. The system of claim 1, wherein the at least one processor device is further configured to recognize characters defined by 10 or less pixels.

7. The system of claim 1, wherein the at least one processor device is further configured to recognize characters defined by 6 or less pixels.

8. The system of claim 1, wherein the at least one processor device is further configured to initiate the audible presentation of the first portion in less than 4 seconds from initiating the optical character recognition to recognize the first portion.

9. The system of claim 1, wherein the at least one processor device is further configured to initiate the audible presentation of the first portion in less than 2 seconds from initiating the optical character recognition to recognize the first portion.

10. The system of claim 1, wherein the at least one processor device is further configured to initiate the audible presentation of the first portion in less than 1 second from initiating the optical character recognition to recognize the first portion.

11. The system of claim 1, wherein the at least one image includes at least two images of the first portion of the text.

12. The system of claim 11, wherein the at least one processor device is further configured to initiate optical character recognition on the at least two images to recognize the first portion, and to combine optical character recognition results from the at least two images in recognizing the first portion.

13. The system of claim 11, wherein the at least one processor device is further configured to initiate optical character recognition on at least two images to recognize the second portion, and wherein none of at least two images includes all of the second portion.

14. The system of claim 11, wherein the at least two images includes a first image in a first resolution and at least one second image in a second, higher resolution, and wherein the at least one processor device is further configured to initiate a first optical character recognition on the first image to recognize the first portion, and if the first optical character recognition fails, initiate a second optical character recognition on the at least one second image to recognize the first portion.

15. The system of claim 14, wherein the at least one processor device is further configured to initiate the second optical character recognition only on a part of the at least one second image to recognize a specific part of the first portion.

16. A system for processing text, the system comprising:
    a memory; and
    at least one processor device configured to:
        receive at least one image capturing an environment of a user, wherein the at least one image includes text to be audibly read;
        initiate optical character recognition to recognize the text;
        store in the memory a first plurality of words associated with a recognized part of the text;
        during the optical character recognition of the text, determine that an operational time of the optical character recognition exceeds a predetermined threshold;
        after determining that the operational time of the optical character recognition exceeds the predetermined threshold, initiate an audible presentation of the first plurality of words corresponding to a first portion of the text that has been recognized and stored in the memory;
        during the audible presentation of the at least part of the first portion, simultaneously perform optical character recognition to recognize a second portion of the text and store in the memory a second plurality of words associated with the second portion; and
        automatically cause the second plurality of words to be audibly presented immediately upon completion of the audible presentation of the first plurality of words.

17. The system of claim 16, wherein the at least one processor device is further configured to delete the first plurality of words from the memory after the audible presentation of the first plurality of words is completed.

18. The system of claim 16, wherein the optical character recognition includes comparing a plurality of sets of image regions proximate to each other, and based on statistics related to the plurality of the sets, recognizing an associated character.

19. The system of claim 16, wherein a background of the text in the at least one image includes at least two different colors.

20. The system of claim 16, wherein the text in the at least one image is in two different colors.

21. A method for accelerating machine reading of text, the method comprising:
    receiving from a mobile image sensor at least one image of text to be audibly read;
    initiating optical character recognition to recognize the text;

during the optical character recognition of the text, determining that an operational time of the optical character recognition exceeds a predetermined threshold;

after determining that the operational time of the optical character recognition exceeds the predetermined threshold, initiating an audible presentation of a first portion of the text that has been recognized;

during the audible presentation of at least part of the first portion, simultaneously performing optical character recognition to recognize a second portion of the text; and automatically causing the second portion of the text to be audibly presented immediately upon completion of the audible presentation of the first portion.

22. A software product stored on a non-transitory computer readable medium and comprising data and computer implementable instructions for carrying out the method of claim 21.

* * * * *